US011674186B2

(12) United States Patent
Tyler et al.

(10) Patent No.: US 11,674,186 B2
(45) **Date of Patent: *Jun. 13, 2023**

(54) SYNTHETIC NUCLEIC ACID CONTROL MOLECULES

(71) Applicant: Exact Sciences Corporation, Madison, WI (US)

(72) Inventors: Ilse A. Tyler, Poway, CA (US); Keith Yaeger, Verona, WI (US); Michael J. Domanico, Middleton, WI (US); Hatim Allawi, Middleton, WI (US); Graham P. Lidgard, Middleton, WI (US)

(73) Assignee: Exact Sciences Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/110,985

(22) Filed: Dec. 3, 2020

(65) Prior Publication Data

US 2021/0172023 A1 Jun. 10, 2021

Related U.S. Application Data

(63) Continuation of application No. 16/168,326, filed on Oct. 23, 2018, now Pat. No. 10,889,867, which is a continuation of application No. 15/105,178, filed as application No. PCT/US2014/071460 on Dec. 19, 2014, now Pat. No. 10,138,524.

(60) Provisional application No. 61/918,349, filed on Dec. 19, 2013.

(51) Int. Cl.

| | |
|---|---|
| ***C12Q 1/6886*** | (2018.01) |
| ***C12N 15/11*** | (2006.01) |
| ***C12Q 1/6876*** | (2018.01) |

(52) U.S. Cl.

CPC ............ *C12Q 1/6886* (2013.01); *C12N 15/11* (2013.01); *C12Q 1/6876* (2013.01); *C12Q 2600/154* (2013.01); *C12Q 2600/156* (2013.01); *C12Q 2600/166* (2013.01)

(58) Field of Classification Search

CPC ................ C12Q 1/6886; C12Q 1/6876; C12Q 2600/154; C12Q 2600/156; C12Q 2600/166; C12N 15/11

See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,965,188 | A | 10/1990 | Mullis et al. |
| 5,011,769 | A | 4/1991 | Duck et al. |
| 5,124,246 | A | 6/1992 | Urdea et al. |
| 5,288,609 | A | 2/1994 | Engelhardt et al. |
| 5,338,671 | A | 8/1994 | Scalice et al. |
| 5,352,775 | A | 10/1994 | Albertsen et al. |
| 5,403,711 | A | 4/1995 | Walder et al. |
| 5,409,818 | A | 4/1995 | Davey et al. |
| 5,463,782 | A | 11/1995 | Carlson et al. |
| 5,494,810 | A | 2/1996 | Barany et al. |
| 5,508,169 | A | 4/1996 | Deugau et al. |
| 5,527,676 | A | 6/1996 | Vogelstein et al. |
| 5,624,802 | A | 4/1997 | Urdea et al. |
| 5,639,611 | A | 6/1997 | Wallace et al. |
| 5,648,212 | A | 7/1997 | Albertsen et al. |
| 5,660,988 | A | 8/1997 | Duck et al. |
| 5,670,325 | A | 9/1997 | Lapidus et al. |
| 5,710,264 | A | 1/1998 | Urdea et al. |
| 5,741,650 | A | 4/1998 | Lapidus et al. |
| 5,773,258 | A | 6/1998 | Birch et al. |
| 5,792,614 | A | 8/1998 | Western et al. |
| 5,830,665 | A | 11/1998 | Shuber et al. |
| 5,846,717 | A | 12/1998 | Brow et al. |
| 5,849,481 | A | 12/1998 | Urdea et al. |
| 5,851,770 | A | 12/1998 | Babon et al. |
| 5,882,867 | A | 3/1999 | Ullman et al. |
| 5,888,778 | A | 3/1999 | Shuber |
| 5,914,230 | A | 6/1999 | Liu et al. |
| 5,928,870 | A | 7/1999 | Lapidus et al. |
| 5,952,178 | A | 9/1999 | Lapidus et al. |
| 5,955,263 | A | 9/1999 | Vogelstein et al. |
| 5,958,692 | A | 9/1999 | Cotton et al. |
| 5,965,408 | A | 10/1999 | Short |
| 5,985,557 | A | 11/1999 | Prudent et al. |
| 5,994,069 | A | 11/1999 | Hall et al. |
| 6,001,567 | A | 12/1999 | Brow et al. |
| 6,013,170 | A | 1/2000 | Meade |

(Continued)

FOREIGN PATENT DOCUMENTS

| | | |
|---|---|---|
| EP | 2055790 | 5/2009 |
| WO | WO 2002070755 | 9/2002 |

(Continued)

OTHER PUBLICATIONS

Cold Spring Harbor protocol, 2006, printed on May 9, 2022, 1page. (Year: 2006).*

Ahlquist et al. Next-generation stool DNA test accurately detects colorectal cancer and large adenomas. Gastroenterology. Feb. 2012;142(2):248-56.

Allawi et al., Invader plus method detects herpes simplex virus in cerebrospinal fluid and simultaneously differentiates types 1 and 2, J Clin Microbiol. Sep. 2006;44(9):3443-7.

Ballabio, et al., Screening for steroid sulfatase (STS) gene deletions by multiplex DNA amplification, Human Genetics, 1990, 84(6): 571-573.

(Continued)

*Primary Examiner* — Narayan K Bhat

(74) *Attorney, Agent, or Firm* — Casimir Jones, S.C.; Mary Ann D. Brow

(57) ABSTRACT

The present invention provides synthetic DNA strands that find use as controls or in nucleic acid testing methods. In particular, provided herein are synthetic DNA strands of known composition for use as control molecules in stool DNA testing, e.g., of mutations and/or methylation of DNA isolated from stool samples.

7 Claims, 11 Drawing Sheets

Specification includes a Sequence Listing.

(56) References Cited

U.S. PATENT DOCUMENTS 6,020,137 A 2/2000 Lapidus et al.
RE36,713 E 5/2000 Vogelstein et al.
6,063,573 A 5/2000 Kayyem
6,090,543 A 7/2000 Prudent et al.
6,090,566 A 7/2000 Vogelstein et al.
6,110,677 A 8/2000 Western et al.
6,110,684 A 8/2000 Kemper et al.
6,121,001 A 9/2000 Western et al.
6,143,529 A 11/2000 Lapidus et al.
6,146,828 A 11/2000 Lapidus et al.
6,150,097 A 11/2000 Tyagi et al.
6,183,960 B1 2/2001 Lizardi
6,203,993 B1 3/2001 Shuber et al.
6,210,884 B1 4/2001 Lizardi
6,221,583 B1 4/2001 Kayyem et al.
6,235,502 B1 5/2001 Weissman et al.
6,245,515 B1 6/2001 Vogelstein et al.
6,248,229 B1 6/2001 Meade
6,268,136 B1 7/2001 Shuber et al.
6,280,947 B1 8/2001 Shuber et al.
6,300,077 B1 10/2001 Shuber et al.
6,303,304 B1 10/2001 Shuber et al.
6,351,857 B2 3/2002 Slaon, III et al.
6,406,857 B1 6/2002 Shuber et al.
6,415,455 B1 7/2002 Slaon, III et al.
6,428,964 B1 8/2002 Shuber
6,475,738 B2 11/2002 Shuber et al.
6,482,595 B2 11/2002 Shuber et al.
6,498,012 B2 12/2002 Laken
6,503,718 B2 1/2003 Shuber et al.
6,551,777 B1 4/2003 Shuber et al.
6,586,177 B1 7/2003 Shuber
6,677,312 B1 1/2004 Vogelstein et al.
6,750,020 B2 6/2004 Shuber
6,800,617 B1 10/2004 Vogelstein et al.
6,812,339 B1 11/2004 Venter et al.
6,818,404 B2 11/2004 Shuber
6,844,155 B2 1/2005 Shuber
6,849,403 B1 2/2005 Shuber
6,872,816 B1 3/2005 Hall et al.
6,919,174 B1 7/2005 Shuber
6,964,846 B1 11/2005 Shuber
7,005,266 B2 2/2006 Sprenger-Haussels
7,087,583 B2 8/2006 Vogelstein et al.
7,267,955 B2 9/2007 Vogelstein et al.
7,368,233 B2 5/2008 Shuber et al.
7,432,050 B2 10/2008 Markowitz
7,485,420 B2 2/2009 Markowitz
7,662,594 B2 2/2010 Kong et al.
7,981,612 B2 7/2011 Shuber et al.
8,361,720 B2 1/2013 Oldham-Haltom et al.
8,916,344 B2 12/2014 Zou et al.
9,000,146 B2 4/2015 Bruinsma et al.
9,290,797 B2 3/2016 Oldham-Haltom et al.
10,138,524 B2 11/2018 Tyler et al.
10,253,358 B2 4/2019 Domanico et al.
2004/0241658 A1 12/2004 Barrett et al.
2005/0089870 A1* 4/2005 Matsubara ........... C12Q 1/6827 435/6.12
2007/0122818 A1 5/2007 Mazumder et al.
2007/0202525 A1 8/2007 Quake et al.
2008/0102452 A1* 5/2008 Roberts .................. C12N 15/70 435/6.12
2008/0176209 A1 7/2008 Muller et al.
2009/0253142 A1 10/2009 Allawi et al.
2010/0028877 A1* 2/2010 Schatz ................. C12Q 1/6827 435/6.12
2011/0112086 A1 5/2011 Pierre et al.
2012/0122088 A1 5/2012 Zou et al.
2012/0196756 A1 8/2012 Ahlquist et al.
2012/0288868 A1 11/2012 Bruinsma et al.
2013/0143216 A1 6/2013 Oldham-Haltom et al.
2013/0231256 A1 9/2013 Oldham-Haltom et al.
2016/0273030 A1 9/2016 Domanico et al.
2016/0312299 A1 10/2016 Tyler et al.
2019/0144948 A1 5/2019 Tyler et al.

FOREIGN PATENT DOCUMENTS

WO WO 2005023091 3/2005
WO WO 2005042713 5/2005
WO WO 2005086938 9/2005
WO WO 2015095689 6/2015

OTHER PUBLICATIONS

Barnay, Genetic disease detection and DNA amplification using cloned thermostable ligase. Proc Natl Acad Sci USA. Jan. 1, 1991;88(1):189-93.

Bustin, Absolute quantification of mRNA using real-time reverse transcription polymerase chain reaction assays. J Mol Endocrinol. Oct. 2000;25(2):169-93.

Ceska et al., Structure-specific DNA cleavage by 5' nucleases, Trends Biochem Sci. Sep. 1998;23(9):331-6.

Chamberlain et al., Deletion screening of the Duchenne muscular dystrophy locus via multiplex DNA amplification. Nucleic Acids Res. Dec. 9, 1988;16(23):11141-56.

Chial, Proto-oncogenes to oncogenes to cancer. Nature Education, 2008;1(1):33.

Coll et al., Evaluation of a rapid method of extracting DNA from stool samples for use in hybridization assays, J Clin Microbiol. Oct. 1989;27(10):2245-8.

Cwirla et al., Peptides on phage: a vast library of peptides for identifying ligands. Proc Natl Acad Sci U S A. Aug. 1990;87(16):6378-82.

Diehl et al., Analysis of mutations in DNA isolated from plasma and stool of colorectal cancer patients. Gastroenterology. Aug. 2008;135(2):489-98.

Diffenbach and Dveksler, PCR Primer, A Laboratory Manual, Cold Spring Harbor Press 1995, TOC Only.

Don et al., ‘Touchdown’ PCR to circumvent spurious priming during gene amplification. Nucleic Acids Research, 1991, 19(14):4008.

Exact Sciences Corp., Cologuard Physician Brochure. Oct. 29, 2010, 14 pages.

Google Search for Cologuard Physician Brochure. Performed Jun. 26, 2017, 1 page.

Grafodatskaya et al., EBV transformation and cell culturing destabilizes DNA methylation in human lymphoblastoid cell lines. Genomics. Feb. 2010;95(2):73-83.

Guilfoyle et al., Ligation-mediated PCR amplification of specific fragments from a class-II restriction endonuclease total digest. Nucleic Acids Res. May 1, 1997;25(9):1854-8.

Hall et al., Sensitive detection of DNA polymorphisms by the serial invasive signal amplification reaction Proc Natl Acad Sci U S A. Jul. 18, 2000;97(15):8272-7.

Hayden et al., Multiplex-Ready PCR: A new method for multiplexed SSR and SNP genotyping. BMC Genomics. Feb. 18, 2008;9:80.

Hecker et al., High and low annealing temperatures increase both specificity and yield in touchdown and stepdown PCR, Biotechniques, 1996, 20(3):478-485.

Herman et al., Methylation-specific PCR: a novel PCR assay for methylation status of CpG islands, PNAS, 1996, 93(13):9821-9826.

Higuchi et al., A general method of in vitro preparation and specific mutagenesis of DNA fragments: study of protein and DNA interactions, Nucleic Acids Research, 1988, 16(15):7351-7367.

Higuchi et al.,Kinetic PCR analysis: real-time monitoring of DNA amplification reactions, Biotechnology, 1993, 11:1026-1030.

Higuchi et al., Simultaneous amplification and detection of specific DNA sequences, Biotechnology, 1992, 10:413-417.

Kaiser et al., A comparison of eubacterial and archaeal structure-specific 5'-exonucleases. J Biol Chem. Jul. 23, 1999;274(30):21387-94.

Kalinina et al., Nanoliter scale PCR with TaqMan detection, Nucleic Acids Research, 1997, 25:1999-2004.

(56) References Cited

OTHER PUBLICATIONS

Lage et al., Whole genome analysis of genetic alterations in small DNA samples using hyperbranched strand displacement amplification and array-CGH, Genome Res. Feb. 2003;13(2):294-307.
Liu et al., Flap endonuclease 1: a central component of DNA metabolism, Annu Rev Biochem. 2004;73:589-615.
Lyamichev et al., Polymorphism identification and quantitative detection of genomic DNA by invasive cleavage of oligonucleotide probes, Nat. Biotech., 1999, 17:292-296.
Nollau et al., Isolation of DNA from stool and bodily fluids for PCR amplification, Biotechniques. May 1996;20(5):784-8.
Olivier, The Invader assay for SNP genotyping, Mutat Res. Jun. 3, 2005;573(1-2):103-10.
Orpana, Fluorescence resonance energy transfer (FRET) using ssDNA binding fluorescent dye, Biomol Eng. Apr. 2004;21(2):45-50.
Rapley, The Nucleic Acid Protocols Handbook (2000), Humana Press, Totowa, N.J, TOC Only.
Roux, Using mismatched primer-template pairs in touchdown PCR, Biotechniques, 1994, 16(5):812-814.
Ryan et al., Non-PCR-dependent detection of the factor V Leiden mutation from genomic DNA using a homogeneous invader microtiter plate assay., Mol Diagn. Jun. 1999;4(2):135-44.
Saferali et al., Cell culture-induced aberrant methylation of the imprinted IG DMR in human lymphoblastoid cell lines. Epigenetics. Jan. 1, 2010;5(1):50-60.
Kwok et al., Effects of primer-template mismatches on the polymerase chain reaction: human immunodeficiency virus type 1 model studies. Nucleic Acids Res. Feb. 25, 1990;18(4):999-1005.
Schouten et al., Relative quantification of 40 nucleic acid sequences by multiplex ligation-dependent probe amplification, Nucleic Acids Research, 2002, 30(12): e57.
Selvin, Fluorescence resonance energy transfer, 1995, Methods Enzymol. 1995;246:300-34.
Sidransky et al., Identification of ras oncogene mutations in the stool of patients with curable colorectal tumors., Science. Apr. 3, 1992;256(5053):102-5.
Stryer, Fluorescence energy transfer as a spectroscopic ruler, Annu Rev Biochem. 1978;47:819-46.
Sugawara et al., Comprehensive DNA methylation analysis of human peripheral blood leukocytes and lymphoblastoid cell lines. Epigenetics. Apr. 2011;6(4):508-15.
Triglia et al., A procedure for in vitro amplification of DNA segments that lie outside the boundaries of known sequences, Nucleic Acids Res., 1988, 16:8186.
Villa et al., Identification of subjects at risk for colorectal carcinoma through a test based on K-ras determination in the stool, Gastroenterology. May 1996;110(5):1346-53.
Vogelstein et al., Digital PCR, PNAS, 1999, 96: 9236-41.
Zou et al., Quantification of methylated markers with a multiplex methylation-specific technology, Clin Chem. Feb. 2012;58(2):375-8.
International Search Report and Written Opinion for PCT/US2014/071460, dated May 28, 2015, 17 pages.
European Search Report for EP14872569.0, dated Jul. 18, 2017, 14 pages.
Communication of the Boards of Appeal, EP Preliminary Opinion dated Oct. 12, 2022 for EP 14872569.0. 14 pages.

* cited by examiner

FIG. 5

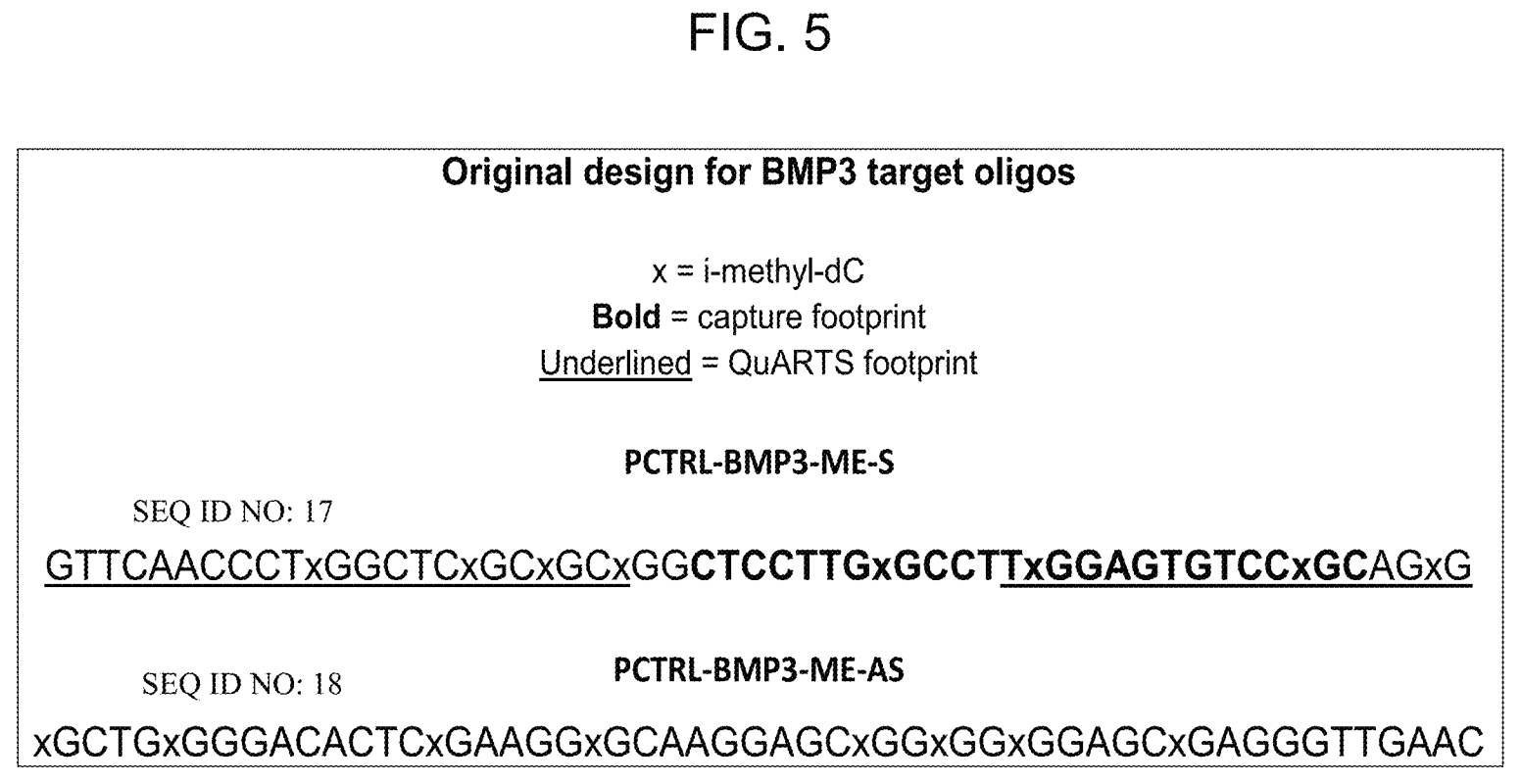

Original design for BMP3 target oligos x = i-methyl-dC
Bold = capture footprint
Underlined = QuARTS footprint

PCTRL-BMP3-ME-S

SEQ ID NO: 17

GTTCAACCCTxGGCTCxGCxGCxGGCTCCTTGxGCCTTxGGAGTGTCCxGCAGxG

PCTRL-BMP3-ME-AS

SEQ ID NO: 18 xGCTGxGGGACACTCxGAAGGxGCAAGGAGCxGGxGGxGGAGCxGAGGGTTGAAC

FIG. 6A

| Oligo Name | Sequence 5' to 3' | Note | SEQ ID NO: |
|---|---|---|---|
| PCTRL-KRAS-38A-S | ACATTTTCATTATTTTTATTATAAGGCCTGCTGAAAATGACTGAATATAAACTTGTGGTAGTTGGAGCTGGTGACGTAGGCAAGAGTGCCTTGACGATACAGCTAATTCAGAATCATTTTGTGGACGAATATGATCCAACAATAGAGGTAAATC | | 1 |
| PCTRL-KRAS-38A-AS | GATTTACCTCTATTGTTGGATCATATTCGTCCACAAAATGATTCTGAATTAGCTGTATCGTCAAGGCACTCTTGCCTACGTCACCAGCTCCAACTACCACAAGTTTATATTCAGTCATTTTCAGCAGGCCTTATAATAAAAATAATGAAAATGT | | 2 |
| PCTRL-KRAS-35C-S | ACATTTTCATTATTTTTATTATAAGGCCTGCTGAAAATGACTGAATATAAACTTGTGGTAGTTGGAGCTGCTGGCGTAGGCAAGAGTGCCTTGACGATACAGCTAATTCAGAATCATTTTGTGGACGAATATGATCCAACAATAGAGGTAAATC | | 3 |
| PCTRL-KRAS-35C-AS | GATTTACCTCTATTGTTGGATCATATTCGTCCACAAAATGATTCTGAATTAGCTGTATCGTCAAGGCACTCTTGCCTACGCCAGCAGCTCCAACTACCACAAGTTTATATTCAGTCATTTTCAGCAGGCCTTATAATAAAAATAATGAAAATGT | | 4 |
| PCTRL-ACTB-WT-S | TTTGTCTCTCTGACTAGGTGTCTAAGACAGTGTTGTGGGTGTAGGTACTAACACTGGCTCGTGTGACAAGGCCATGAGGCTGGTGTAAAGCGGCCTTGGAGTGTGTATTAAGTAGGTGCACAGTAG | | 5 |
| PCTRL-ACTB-WT-AS | CTACTGTGCACCTACTTAATACACACTCCAAGGCCGCTTTACACCAGCCTCATGGCCTTGTCACACGAGCCAGTGTTAGTACCTACACCCACAACACTGTCTTAGACACCTAGTCAGAGAGACAAA | | 6 |
| PCTRL-KRAS-WT-S | ACATTTTCATTATTTTTATTATAAGGCCTGCTGAAAATGACTGAATATAAACTTGTGGTAGTTGGAGCTGGTGGCGTAGGCAAGAGTGCCTTGACGATACAGCTAATTCAGAATCATTTTGTGGACGAATATGATCCAACAATAGAGGTAAATC | | 7 |
| PCTRL-KRAS-WT-AS | GATTTACCTCTATTGTTGGATCATATTCGTCCACAAAATGATTCTGAATTAGCTGTATCGTCAAGGCACTCTTGCCTACGCCACCAGCTCCAACTACCACAAGTTTATATTCAGTCATTTTCAGCAGGCCTTATAATAAAAATAATGAAAATGT | | 8 |

FIG. 6B

| Oligo Name | Sequence 5' to 3' | Note | SEQ ID NO: |
|---|---|---|---|
| PCTRL-126-NDRG4-ME-S | GGGTGTCCCCCAGGCTCCGCGTCGXGGTCCCXGCTXG<br>CCCTCCXGCCXGCCCACXGGGCACCCCAGCXGXGCAG<br>AAGGXGGAAGCCAXGXGXGAGGGACCGCGGTCCGTCC<br>GGGACTAGCCCCAGG | X=5-Me-dC | 9 |
| PCTRL-126-NDRG4-ME-AS | CCTGGGGCTAGTCCCGGACGGACCGCGGTCCCTXGXG<br>XGTGGCTTCXGCCTTCTGXGXGGCTGGGGTGCCXGGT<br>GGGXGGGXGGGAGGGXGAGXGGGGACXGCGACGCGGA<br>GCCTGGGGGACACCC | X=5-Me-dC | 10 |
| PCTRL-126-BMP3-ME-S | CGGGCTCCGTGCGCCCTCGCCCCAGCTGGTTTGGAGT<br>TCAACCCTXGGCTCXGCXGCXGGCTCCTTGXGCCTTX<br>GGAGTGTCCXGCAGXGACGCCGGGAGCCGACGCGCCG<br>CGCGGGTACCTAGCC | X=5-Me-dC | 11 |
| PCTRL-126-BMP3-ME-AS | GGCTAGGTACCCGCGCGGCGCGTCGGCTCCCGGCGTX<br>GCTGXGGGACACTCXGAAGGXGCAAGGAGCXGGXGGX<br>GGAGCXGAGGGTTGAACTCCAAACCAGCTGGGGCGAG<br>GGCGCACGGAGCCCG | X=5-Me-dC | 12 |
| PCTRL-126-NDRG4-WT-S | GGGTGTCCCCCAGGCTCCGCGTCGCGGTCCCCGCTCG<br>CCCTCCCGCCCGCCCACCGGGCACCCCAGCCGCGCAG<br>AAGGCGGAAGCCACGCGCGAGGGACCGCGGTCCGTCC<br>GGGACTAGCCCCAGG | | 13 |
| PCTRL-126-NDRG4-WT-AS | CCTGGGGCTAGTCCCGGACGGACCGCGGTCCCTCGCG<br>CGTGGCTTCCGCCTTCTGCGCGGCTGGGGTGCCCGGT<br>GGGCGGGCGGGAGGGCGAGCGGGGACCGCGACGCGGA<br>GCCTGGGGGACACCC | | 14 |
| PCTRL-126-BMP3-WT-S | CGGGCTCCGTGCGCCCTCGCCCCAGCTGGTTTGGAGT<br>TCAACCCTCGGCTCCGCCGCCGGCTCCTTGCGCCTTC<br>GGAGTGTCCCGCAGCGACGCCGGGAGCCGACGCGCCG<br>CGCGGGTACCTAGCC | | 15 |
| PCTRL-126-BMP3-WT-AS | GGCTAGGTACCCGCGCGGCGCGTCGGCTCCCGGCGTC<br>GCTGCCGGACACTCCCAACGCGCAAGGACCCGGCGGC<br>GGAGCCGAGGGTTGAACTCCAAACCAGCTGGGGCGAG<br>GGCGCACGGAGCCCG | | 16 |

FIG. 8

*DNA Control 3, Negative*
*lot specific run validity specifications for ACT log strands*
*lower specification = 3.69*
*upper specification = 4.69*

| **DNA Control Performance at +/- 10%**<br>DNA Control 3 ACT | | | |
|---|---|---|---|
| **Percentage DNA Control into *Cologuard* Assay** | **Log Strands ACT Result** | **Method for determining log strands ACT** | **Run Validity Specifications MET/NOT MET** |
| 85% | 4.310 | Empirical mean | MET |
| 90% | 4.334 | Calculated estimate | MET |
| 100% | 4.380 | Empirical mean | MET |
| 110% | 4.448 | Calculated estimate | MET |
| 115% | 4.481 | Empirical mean | MET |

Bivariate fit of log(strands) ACT by volume% DNA Control=DNA Control 3, Negative, lot designation=3

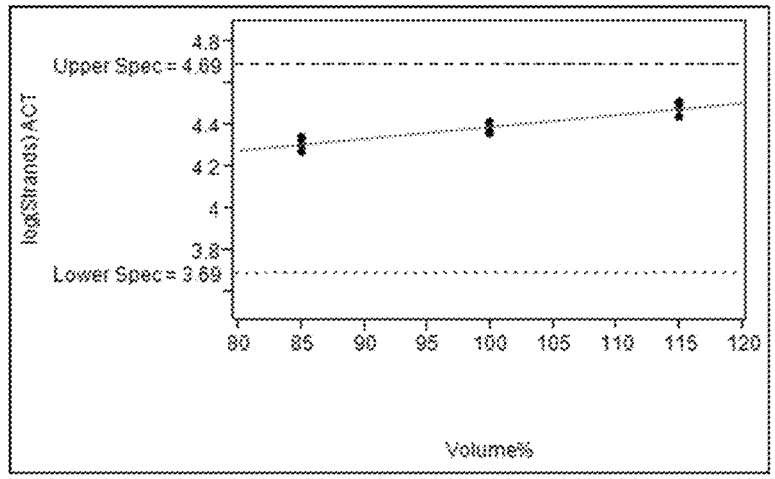

*LINEAR FIT*

*LOG(STRANDS) ACT = 3.8207537 + 0.0056981*VOLUME%*

*SUMMARY OF FIT*

| | |
|---|---|
| *RSquare* | *0.865969* |
| *RSquare Adj* | *0.852566* |
| *Root Mean Square Error* | *0.030076* |
| *Mean of Response* | *4.390561* |
| *Observations (or Sum Wgts)* | *12* |

SYNTHETIC NUCLEIC ACID CONTROL MOLECULES

The present application is a continuation of U.S. patent application Ser. No. 16/168,326, filed Oct. 23, 2018, now allowed, which is a continuation of U.S. patent application Ser. No. 15/105,178, filed Jun. 16, 2016, now U.S. Pat. No. 10,138,524, which is a § 371 U.S. National Entry of International Patent Application PCT/US2014/071460, filed Dec. 19, 2014, which claims priority to U.S. Provisional Application Ser. No. 61/918,349, filed Dec. 19, 2013, each of which is incorporated herein by reference.

FIELD

The present invention provides synthetic DNA strands that find use as controls or in nucleic acid testing methods. In particular, provided herein are DNA strands for use as control molecules in stool DNA testing, e.g., of mutations and/or methylation of DNA isolated from stool samples.

BACKGROUND

Nucleic acids from stool samples that are analyzed for the presence of mutations and/or for methylation status associated with disease or risk of disease typically pass through a number of process steps during analysis. These steps may comprise, e.g., filtration, precipitation, capture, washing, elution, and/or chemical modification. For analysis of DNAs to determine methylation status, processing typically comprises treatment with bisulfite to covert unmethylated dC bases to dU residues, making them more readily distinguishable from the methyl-C residues that are protected from bisulfite conversion.

Sample processing steps can be evaluated for efficiency and efficacy by the use of control DNAs of known composition. For mutation detection assays, plasmid DNAs containing cloned DNA fragments containing wild type and mutant sequences may be used, for example. For analysis of methylation of control DNAs, however, plasmid DNA cannot be used as the bacterial host cells typically used to grow plasmids do not methylate C residues in the same manner as would be found in mammalian cells. Treatment of DNA after isolation, e.g., with a DNA methylase, also cannot reliably reproduce DNA having a degree and pattern of methylation accurately reflecting actual target DNA. Thus, there is a need for synthetic nucleic acid compositions that can act as accurate controls for stool-derived target DNAs through all of the steps of processing and detection.

SUMMARY

The present invention provides DNA homologs (controls) that resemble targeted DNA and that undergo normal testing and processing to control and provide a normal range of results for nucleic acid detection assays. These DNA controls are referred to as run controls and they serve as indicators for assay performance and validity at each process step. The run controls also provide insights into assay performance, making it possible to detect, e.g., operator, systematic, and/or instrumentation errors. The run control DNAs provided herein find use as DNA targets that undergo the entire assay process, e.g., from isolation/capture, through setup, reaction, and detection assay.

Some embodiments of the technology provide run control reagents, e.g., comprising one or more of the run control DNAs. For example, in some embodiments controls are supplied at an aliquot volume that matches, substantially matches, approximates, and/or essentially matches an actual sample (e.g., a stool sample or a sample derived from and/or produced from a stool sample); in some embodiments, controls are supplied as a concentrated stock accompanied with a dilution buffer for preparation of the proper volume prior to use (e.g., a volume that matches, substantially matches, approximates, and/or essentially matches an actual sample (e.g., a stool sample or a sample derived from and/or produced from a stool sample)). The control reagents are not limited in the volume at which they are used. For example, in some embodiments controls are supplied at a target fill volume of 1 to 25 mL, e.g., 10 to 20 mL, e.g., a target fill volume of 10, 11, 12, 13, 14, 15, 16, 17, 18, 19, or 20 mL, e.g., in some embodiments, a target fill volume of approximately 16.5 mL.

The controls are designed to indicate if the sample processing procedures (e.g., DNA isolation, methyl conversion, and/or purification) were completed successfully. In some embodiments, controls contain capture footprint sequences and methylation assay (e.g., QuARTS assay) footprint sequences. A capture footprint or a capture footprint sequence refers to a sequence that provides for the capture of the DNA comprising the capture footprint by a capture probe (e.g., an oligonucleotide complementary to the capture footprint and, in some embodiments, linked to a solid support, e.g., a bead, magnetic bead, etc.). A methylation assay footprint refers to a sequence that is tested for methylation status by a methylation assay (e.g., a QuARTS assay), e.g., a sequence comprising one or more CpG dinucleotides, wherein the C is methylation or unmethylated, to test for methylation status by use of the methylation assay.

In some embodiments, methylation targets comprise methylcytosine bases for protection against bisulfate conversion to allow detection in the QUARTS assay. In some embodiments, targets representing methylated markers are fully methylated and are quantifiable. In some embodiments, targets representing KRAS mutation markers are quantifiable. In some embodiments, controls are processed through one or more steps including, but not limited to, DNA isolation (e.g., capture, e.g., by a capture probe and/or substrate), bisulfite conversion, sample clean-up, and/or methylation detection, e.g., by QUARTS.

In some embodiments, DNA targets are similar in size to stool DNA, e.g., 100 to 1000 bp, e.g., 100, 150, 200, 250, 300, 350, 400, 450, 500, 550, 600, 650, 700, 750, 800, 850, 900, 950, or 1000 bp. In some embodiments, the DNA targets are double stranded.

In some embodiments, the matrix (e.g., sample buffer and other non-control DNA components such as background DNA, etc.) mimics stool sample performance.

In some embodiments, controls are provided that correspond to high, low, and negative outcomes of a test performed on a stool sample being screened for biomarkers (e.g., targets) associated with colorectal cancer. For example, some embodiments provide a High Control comprising a high amount of beta actin target, a high amount of the methylation target (e.g., comprising DNA comprising a high % of methylation), and a high amount of the mutation target (e.g., comprising DNA comprising a high % of mutant sequence). Some embodiments provide a Low Control comprising a high amount of beta actin, a low amount of the methylation target (e.g., comprising DNA comprising a low % of methylation), and a low amount of the mutation target (e.g., comprising DNA comprising a low % of the mutant sequence). Some embodiments provide a Negative Control comprising a low amount of beta actin, no (e.g., undetectable) methylation target (e.g., comprising DNA comprising 0% methylation or comprising substantially or essentially 0% methylation), and no (e.g., undetectable) mutation target (e.g., comprising DNA comprising 0% of the mutant sequence or comprising substantially or essentially 0% of the mutant sequence). High and low are defined in terms of relation to the normal range of signal in positive samples associated with colorectal cancer.

In some embodiments, controls comprise targets to generate multiple types of signals. For example, some embodiments provide controls that are detectable at a plurality of wavelengths, e.g., by a detector of electromagnetic radiation. Some embodiments provide controls comprising a plurality of fluorescent dyes, each having a characteristic emission detectable by fluorimetry. In some embodiments, controls contain targets for each dye channel used in the methylation and mutation assay (e.g. QuARTS assay). In some embodiments, controls produce signals in the Quasar, FAM, and/or HEX dye channels. For example, in some embodiments the methylation assay detects the methylation of ACTB, NDRG4, and BMP3 by monitoring signals produced in the Quasar, FAM, and HEX channels, and mutation assays monitor ACTB, KRAS 38A, and KRAS 35C in the Quasar, FAM, and HEX channels. The technology is not limited to these dyes, these fluorescence, channels, or these combinations thereof.

In some embodiments, controls provide adequate signal in the methylation assay (e.g., QuARTS assay) when +/−10% (e.g., within 1%, 2%, 3%, 4%, 6%, 6%, 7%, 8%, 9%, or 10%) of the recommended control volume is utilized and processed correctly. In some embodiments, controls provide adequate signal to meet run validity criteria when processed at +/−15% (e.g., within 1%, 2%, 3%, 4%, 6%, 6%, 7%, 8%, 9%, 10%, 11%, 12%, 13%, 14%, or 15%) of the recommended volume.

In some embodiments, control reagents are provided in vessels (e.g., tubes, capsules, ampules, bottles, bags, boxes, jars, etc.) to prevent controls from being used incorrectly (e.g. comprising different color caps, barcoding, or other marking options).

In some embodiments, the controls have a failure rate≤1% (e.g., 0% to 1%) when processed according to instructions for use.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

FIG. 1A shows a plot of the size distribution of genomic DNA sheared by passage through a 26 ½ gauge needle (needle sheared) 10 times. FIG. 1B shows a plot of the size distribution of genomic DNA fragmented by sonication using a Covaris S2 sonicator.

FIG. 2A shows the structure of deoxycytosine. FIG. 2B shows the structure of 5-methyl-deoxycytosine. FIG. 2C shows the in vivo reaction catalyzed by methyltransferase and using a S-adenosyl methionine cofactor (e.g., SAH, S-adenosyl homocysteine with a reactive methyl group) for conversion of the deoxycytosine base in a strand of a nucleic acid (e.g., a DNA) to a 5-methyl-deoxycytosine base in the strand of nucleic acid (e.g., a DNA).

FIG. 5 shows the sequences of an embodiment of a BMP3 target oligonucleotide produced as described herein. An "x" denotes i-methyl-dC; bold bases in the sequence denote the capture footprint; underlined bases in the sequence denote the QuARTS assay footprint.

FIGS. 6A and 6B are a table showing the sequences of oligonucleotides produced in accordance with the technology provided herein. FIG. 6 provides other data for the oligonucleotides. including positions of methyl-cytosines (X), molecular weight, length, and name.

FIG. 8 is a plot showing that embodiments of the DNA controls provide adequate signal when processed with +/−15% of the required volume.

DEFINITIONS

Figure 1A:
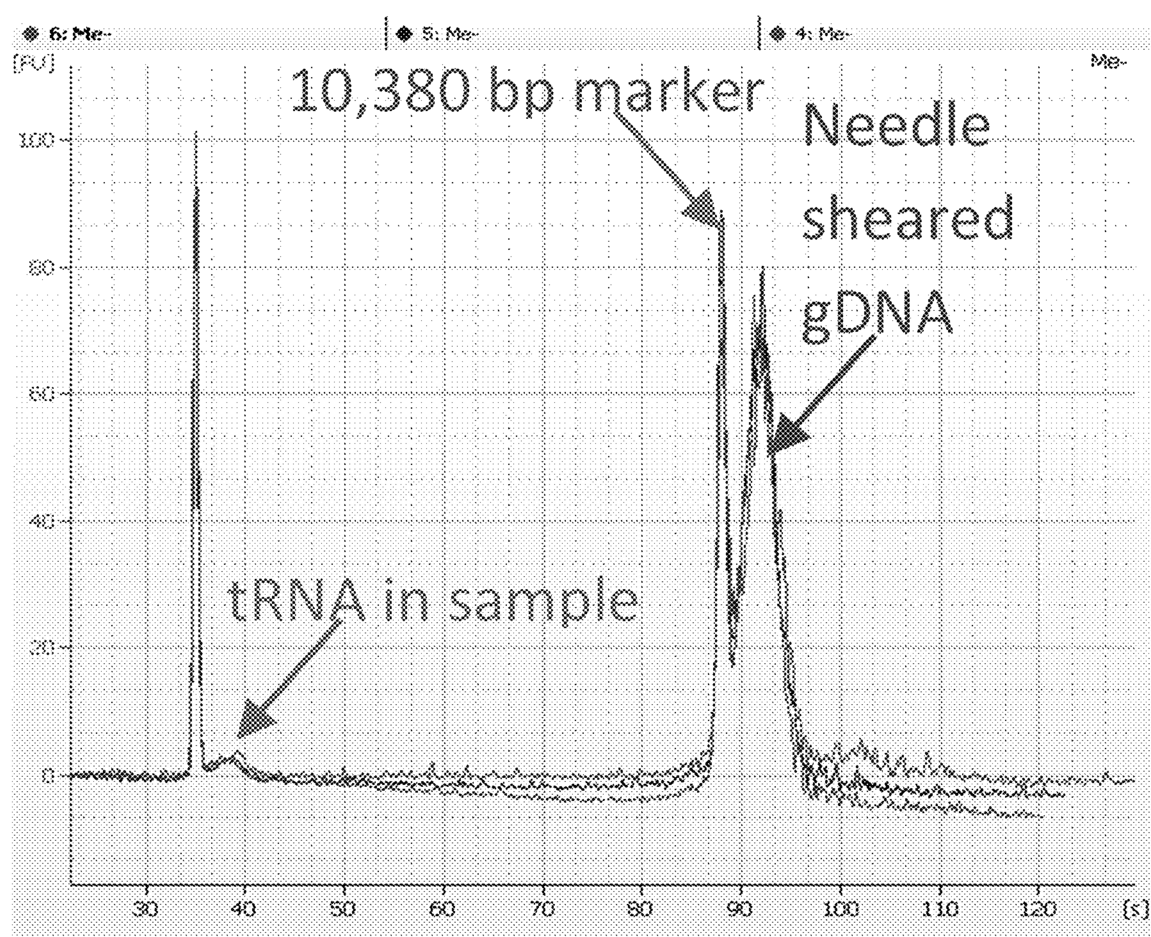
FIGS. 1A and 1B provide a series of plots showing the size distribution of fragmented genomic DNA as measured by a Bioanalyzer (Agilent Technologies).

To facilitate an understanding of the present technology, a number of terms and phrases are defined below. Additional definitions are set forth throughout the detailed description.

The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

As used herein, "a" or "an" or "the" can mean one or more than one. For example, "a" widget can mean one widget or a plurality of widgets.

As used herein, the term "analyte" is to be construed broadly as any compound, molecule, element, ion, or other substance of interest to be detected, identified, or characterized.

As used herein, the terms "subject" and "patient" refer to an animal, preferably a human, from which a stool specimen is collected. In some instances, the subject is also a "user" (and thus the user is also the subject or patient).

The term "sample" as used herein is used in its broadest sense. For example, a sample relates to a material or mixture of materials, typically, although not necessarily, in liquid form, containing one or more analytes of interest. A sample may be obtained from a biological, environmental, or synthetic source. In particular embodiments, a sample is suspected of containing a human gene or chromosome or sequences (e.g., fragments) associated with a human chromosome. Samples may comprise a cell, chromosomes isolated from a cell (e.g., a spread of metaphase chromosomes), genomic DNA (e.g., in solution or bound to a solid support), RNA (e.g., in solution or bound to a solid support), cDNA (e.g., in solution or bound to a solid support), and the like. A sample may contain contaminants (e.g., non-target nucleic acid, proteins, small molecules, biological or environmental matter, etc.) or may be in a purified or semi-purified form.

The term "target," when used in reference to a nucleic acid detection or analysis method herein, refers to a nucleic acid having a particular sequence of nucleotides to be detected or analyzed, e.g., in a sample or reaction mixture suspected of containing the target nucleic acid. In some embodiments, a target is a nucleic acid having a particular non-wild-type sequence (e.g., a mutant sequence (e.g., a point mutation relative to wild-type)) or a sequence for which it is desirable to determine a methylation status. When used in reference to the polymerase chain reaction, "target" generally refers to the region of nucleic acid bounded by the primers used for polymerase chain reaction. Thus, the "target" is sought to be sorted out from other nucleic acid sequences that may be present in a sample. A "target amplicon" is a nucleic acid generated by amplification (e.g., PCR amplification) of a target sequence. The term "sample template" refers to nucleic acid originating from a sample that is analyzed for the presence of a target.

The term "control" as used herein refers to nucleic acid having known features (e.g., known sequence (e.g., wild-type, mutant, allele, etc.), known concentration, known formulation, known modification (e.g., methylation)) for use in comparison to an experimental target (e.g., a nucleic acid of unknown sequence (e.g., wild-type, mutant, allele, etc.), unknown concentration, unknown formulation, unknown modification (e.g., methylation)). In quantitative assays such as qPCR, QUARTS assay, etc., a "calibrator" or "calibration control" is a nucleic acid of known sequence, e.g., having the same sequence as a portion of an experimental target nucleic acid, and a known concentration or series of concentrations (e.g., a serially diluted control target for generation of calibration curved in quantitative PCR).

As used herein, the term "vector" refers to a nucleic acid into which a foreign nucleic acid fragment may be ligated, and that can be stably maintained and propagated in a host organism (e.g., in *E. coli* or another bacterial strain; in *S. cerevesiae* or another fungal strain).

As used herein, the term "locus" refers to a particular position (e.g., of a mutation, polymorphism, or a C residue in a CpG dinucleotide, etc.) within a defined region or segment of a nucleic acid, such as a gene or any other characterized sequence on a chromosome or RNA molecule. A locus is not limited to any particular size or length and may refer to a portion of a chromosome, a gene, a functional genetic element, or a single nucleotide or base pair. As used herein in reference to CpG sites that may be methylated, a locus refers to the C residue in the CpG dinucleotide. As used herein in reference to a position that may be mutated (e.g., KRAS G35T, etc.), a locus refers to the nucleotide (or nucleotides) or base pair (or base pairs) that may either be in wild-type or mutant form.

As used herein, "methylation" or "methylated," as used in reference to the methylation status of a cytosine, e.g., in a CpG dinucleotide locus, generally refers to the presence or absence of a methyl group at position 5 of the cytosine residue (i.e., indicating whether a particular cytosine is 5-methylcytosine). Methylation may be determined directly, e.g., as evidenced by routine methods for analysis of the methylation status of cytosines, e.g., by determining the sensitivity (or lack thereof) of a particular C-residue to conversion to uracil by treatment with bisulfite. For example, a cytosine residue in a sample that is not converted to uracil when the sample is treated with bisulfite in a manner that would be expected to convert that residue if non-methylated (e.g., under conditions in which a majority or all of the non-methylated cytosines in the sample are converted to uracils) may generally be deemed "methylated."

As used herein, a nucleic acid having a methylation percentage of 100% indicates that the nucleic acid has a methyl group attached to the C of every CpG dinucleotide, e.g., the nucleic acid is "fully methylated". In addition, as used herein in some contexts, 100% methylation indicates that all instances and/or copies of a particular nucleic acid are fully methylated, e.g., each instance and/or copy of the nucleic acid has a methyl group attached to the C of every CpG dinucleotide. It is to be understood that experimental and/or other reaction conditions for producing a nucleic acid having 100% methylation may, in some embodiments, produce a nucleic acid that has substantially 100% methylation, e.g., an amount of methylation that is lower than 100% and/or approximately 100%, e.g., 90%, 91%, 92%, 93%, 94%, 95%, 96%, 97, 98%, 99%, 99.5%, or 99.9% methylation, either in the extent of methylation of the CpG dinucleotides of each nucleic acid strand and/or in the number of instances and/or copies of each nucleic acid that have 100% methylation.

As used herein, "sensitivity" as used in reference to a diagnostic assay, e.g., a methylation assay, refers to clinical sensitivity. Clinical sensitivity refers to the proportion of positive samples that give a positive result using a diagnostic assay. Sensitivity is generally calculated as the number of true positives identified by the assay divided by the sum of the number of true positives and the number of false negatives determined by the assay on known positive samples. Similarly, the term "specificity" refers to the proportion or number of true negatives determined by the assay divided by the sum of the number of true negatives and the number of false positives determined by the assay on known negative sample(s).

The term "wild-type" refers to a gene, gene product, or fragment thereof that has the characteristics of that gene or gene product when isolated from a naturally occurring source and is of the sequence and/or form that is most frequently observed in a population. In contrast, the terms "modified," "mutant," and/or "variant" refer to a gene, gene product, or a fragment thereof that displays modifications in sequence and or functional properties (i.e., altered characteristics) when compared to wild-type. It is noted that naturally occurring mutants can be isolated; these are identified by the fact that they have altered characteristics when compared to the wild-type gene or gene product.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contain a subportion of the total kit components. The containers may be delivered to the intended recipient together or separately. For example, a first container may contain an enzyme for use in an assay, while a second container contains oligonucleotides. The term "fragmented kit" is intended to encompass kits containing analyte specific reagents (ASRs) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" encompasses both fragmented and combined kits.

As used herein, the term "assay system" refers to the reagents, materials, instruments, etc. for performing an assay, and the particular arrangement thereof (e.g., in a single vessel, in separate vessels, in wells of a microplate, etc.).

As used herein, the term "information" refers to any collection of facts or data. In reference to information stored or processed using a computer system(s), including but not limited to internets, the term refers to any data stored in any format (e.g., analog, digital, optical, etc.). As used herein, the term "information related to a subject" refers to facts or data pertaining to a subject (e.g., a human, plant, or animal). The term "genomic information" refers to information pertaining to a genome including, but not limited to, nucleic acid sequences, genes, ploidy, allele frequencies, RNA expression levels, protein expression, phenotypes correlating to genotypes, etc. "Allele frequency information" refers to facts or data pertaining to allele frequencies, including, but not limited to, allele identities, statistical correlations between the presence of an allele and a characteristic of a subject (e.g., a human subject), the presence or absence of an allele in an individual or population, the percentage likelihood of an allele being present in an individual having one or more particular characteristics, etc. "Methylation status information" refers to facts or data, including, but not limited to, methylation rates, methylation ratios, etc. at one or more specific loci in a subject.

As used herein, the term "colorectal cancer" includes the well-accepted medical definition that defines colorectal cancer as a medical condition characterized by cancer of cells of the intestinal tract below the small intestine (e.g., the large intestine (colon), including the cecum, ascending colon, transverse colon, descending colon, sigmoid colon, and rectum). Additionally, as used herein, the term "colorectal cancer" further includes medical conditions that are characterized by cancer of cells of the duodenum and small intestine (jejunum and ileum).

As used herein, the term "metastasis" refers to the process in which cancer cells originating in one organ or part of the body relocate to another part of the body and continue to replicate. Metastasized cells subsequently form tumors that may further metastasize. Metastasis thus refers to the spread of cancer from the part of the body where it originally occurs to other parts of the body. As used herein, the term "metastasized colorectal cancer cells" refers to colorectal cancer cells that have metastasized, e.g., referring to colorectal cancer cells localized in a part of the body other than the duodenum, small intestine (jejunum and ileum), large intestine (colon), including the cecum, ascending colon, transverse colon, descending colon, sigmoid colon, and rectum.

As used herein, "an individual is suspected of being susceptible to metastasized colorectal cancer" refers to an individual who is at an above-average risk of developing metastasized colorectal cancer. Examples of individuals at a particular risk of developing metastasized colorectal cancer are those whose family medical history indicates above average incidence of colorectal cancer among family members and/or those who have already developed colorectal cancer and have been effectively treated who therefore face a risk of relapse and recurrence. Other factors that may contribute to an above-average risk of developing metastasized colorectal cancer that would thereby lead to the classification of an individual as being suspected of being susceptible to metastasized colorectal cancer may be based upon an individual's specific genetic, medical, and/or behavioral background and characteristics.

The term "neoplasm" as used herein refers to any new and abnormal growth of tissue. Thus, a neoplasm can be a premalignant neoplasm or a malignant neoplasm.

The term "neoplasm-specific marker," as used herein, refers to any biological material or element that can be used to indicate the presence of a neoplasm. Examples of biological materials include, without limitation, nucleic acids, polypeptides, carbohydrates, fatty acids, cellular components (e.g., cell membranes and mitochondria), and whole cells. In some instances, markers are particular nucleic acid regions (e.g., genes, intragenic regions, specific loci, etc.). Regions of nucleic acid that are markers may be referred to, e.g., as "marker genes," "marker regions," "marker sequences," "marker loci," etc.

The term "colorectal neoplasm-specific marker" refers to any biological material that can be used to indicate the presence of a colorectal neoplasm (e.g., a premalignant colorectal neoplasm; a malignant colorectal neoplasm). Examples of colorectal neoplasm-specific markers include, but are not limited to, exfoliated epithelial markers (e.g., bmp-3, bmp-4, SFRP2, vimentin, septin9, ALX4, EYA4, TFPI2, NDRG4, FOXE1, long DNA, BAT-26, K-ras, APC, melanoma antigen gene, p53, BRAF, and PIK3CA) and fecal occult blood markers (e.g., hemoglobin, alpha-defensin, calprotectin, α1-antitrypsin, albumin, MCM2, transferrin, lactoferrin, and lysozyme). For additional markers, see also U.S. Pat. Nos. 7,485,420; 7,432,050; 5,352,775; 5,648,212; U.S. RE36713; U.S. Pat. Nos. 5,527,676; 5,955,263; 6,090,566; 6,245,515; 6,677,312; 6,800,617; 7,087,583; 7,267,955; and U.S. Pat. Pub. 2012/0196756 (see, e.g., Table 1 thereof); each of which is herein incorporated by reference in its entirety.

The term "amplifying" or "amplification" in the context of nucleic acids refers to the production of multiple copies of a polynucleotide, or a portion of the polynucleotide (e.g., a target), typically starting from a small amount of the polynucleotide (e.g., a single polynucleotide molecule, 10 to 100 polynucleotide molecules, 1000 polynucleotide molecules, etc.), where the amplification products or amplicons (e.g., target amplicons) are generally detectable. Amplification of polynucleotides encompasses a variety of chemical and enzymatic processes. The generation of multiple DNA copies from one or a few copies of a target or template DNA molecule during a polymerase chain reaction (PCR; see, e.g., U.S. Pat. Nos. 4,683,195; 4,683,202; and 4,965,188; herein incorporated by reference in their entireties) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S. Pat. No. 7,662,594; herein incorporated by reference in its entirety), hot-start PCR (see, e.g., U.S. Pat. Nos. 5,773,258 and 5,338,671; each herein incorporated by reference in its entirety), intersequence-specfic PCR, inverse PCR (see, e.g., Triglia, et alet al. (1988) Nucleic Acids Res., 16:8186; herein incorporated by reference in its entirety), ligation-mediated PCR (see, e.g., Guilfoyle, R. et alet al., Nucleic Acids Research, 25:1854-1858 (1997); U.S. Pat. No. 5,508,169; each of which is herein incorporated by reference in its entirety), methylation-specific PCR (see, e.g., Herman, et al., (1996) PNAS 93(13) 9821-9826; herein incorporated by reference in its entirety), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which is herein incorporated by reference in its entirety), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, et alet al., (1992) Biotechnology 10:413-417; Higuchi, et al., (1993) Biotechnology 11:1026-1030; each of which is herein incorporated by reference in its entirety), reverse transcription PCR (see, e.g., Bustin, S. A. (2000) J. Molecular Endocrinology 25:169-193; herein incorporated by reference in its entirety), solid phase PCR, thermal asymmetric interlaced PCR, Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which is herein incorporated by reference in its entirety), and digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525; each of which is incorporated herein by reference in its entirety).

As used herein, the term "nucleic acid detection assay" or "detection assay" refers generally to any method of determining the nucleotide composition of all or a portion of a nucleic acid of interest (e.g., sequence and/or methylation status of one or more bases in a nucleic acid). Nucleic acid detection assays include but are not limited to, DNA sequencing methods, probe hybridization methods, structure specific cleavage assays (e.g., the INVADER assay, (Hologic, Inc.) and are described, e.g., in U.S. Pat. Nos. 5,846,717, 5,985,557, 5,994,069, 6,001,567, 6,090,543, and 6,872,816; Lyamichev et al., Nat. Biotech., 17:292 (1999), Hall et al., PNAS, USA, 97:8272 (2000), and US 2009/0253142, each of which is herein incorporated by reference in its entirety for all purposes); enzyme mismatch cleavage methods (e.g., Variagenics, U.S. Pat. Nos. 6,110,684, 5,958,692, 5,851,770, herein incorporated by reference in their entireties); polymerase chain reaction; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210,884, 6,183,960 and 6,235,502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (e.g., Barnay Proc. Natl. Acad Sci. USA 88, 189-93 (1991)); and sandwich hybridization methods (e.g., U.S. Pat. No. 5,288,609, herein incorporated by reference in its entirety). In some embodiments, target nucleic acid is amplified (e.g., by PCR) and amplified nucleic acid is detected simultaneously using an invasive cleavage assay. Assays configured for performing a detection assay (e.g., a flap cleavage assay) in combination with an amplification assay are described in US Patent Publication US 20090253142 A1 (application Ser. No. 12/404,240), incorporated herein by reference in its entirety for all purposes. Additional amplification plus flap cleavage detection configurations, termed the QuARTS method, are described in U.S. Pat. Nos. 8,361,720 and 8,715,937, and U.S. patent application Ser. Nos. 12/946,745 and 13/720,757, all incorporated herein by reference in their entireties for all purposes.

As used herein, the term "PCR reagents" refers to all reagents that are required for performing a polymerase chain reaction (PCR) on a template. As is known in the art, PCR reagents typically include a primer pair (e.g., a first primer and a second primer, a forward primer and a reverse primer, etc.), a thermostable polymerase (e.g., DNA polymerase), and nucleotides (e.g., deoxynucleoside triphosphates). Depending on the polymerase used, ions (e.g., $Mg_2^+$) may also be present (e.g., in the form of salts (e.g., $MgCl_2$). PCR reagents may optionally contain a template from which a target sequence can be amplified.

As used herein, the term "flap assay" refers to an invasive cleavage assay in which a flap oligonucleotide is cleaved in an overlap-dependent manner by a flap endonuclease to release a flap that is then detected. The principles of flap assays are well known and described in, e.g., U.S. Pat. App. No. 2013/0143216; Lyamichev et al., Nat. Biotechnol. 1999 17:292-296; Ryan et al., Mol. Diagn. 1999 4:135-44; Allawi et al., J Clin Microbiol. 2006 44: 3443-3447; herein incorporated by reference in their entireties, and include, e.g., the INVADER and QUARTS assays discussed above. Certain reagents that are employed in a flap assay are described below.

The term "probe oligonucleotide" or "flap oligonucleotide", when used in reference to flap assay, refers to an oligonucleotide that interacts with a target nucleic acid to form a cleavage structure in the presence of an invasive oligonucleotide.

The term "invasive oligonucleotide" refers to an oligonucleotide that hybridizes to a target nucleic acid at a location adjacent to the region of hybridization between a probe and the target nucleic acid, wherein the 3' end of the invasive oligonucleotide comprises a portion (e.g., a chemical moiety, or one or more nucleotides) that overlaps with the region of hybridization between the probe and target. The 3' terminal nucleotide of the invasive oligonucleotide may or may not base pair a nucleotide in the target. In some embodiments, the invasive oligonucleotide contains sequences at its 3' end that are substantially the same as sequences located at the 5' end of a portion of the probe oligonucleotide that anneals to the target strand.

The term "flap endonuclease" or "FEN," as used herein, refers to a class of nucleolytic enzymes, typically 5' nucleases, that act as structure-specific endonucleases on DNA structures with a duplex containing a single stranded 5' overhang, or flap, on one of the strands that is displaced by another strand of nucleic acid (e.g., such that there are overlapping nucleotides at the junction between the single and double-stranded DNA). FENs catalyze hydrolytic cleavage of the phosphodiester bond at the junction of single and double stranded DNA, releasing the overhang, or the flap. Flap endonucleases are reviewed by Ceska and Savers (Trends Biochem. Sci. 1998 23:331-336) and Liu et al (Annu. Rev. Biochem. 2004 73: 589-615; herein incorporated by reference in its entirety). FENs may be individual enzymes, multi-subunit enzymes, or may exist as an activity of another enzyme or protein complex (e.g., a DNA polymerase).

A flap endonuclease may be thermostable. For example, FEN-1 flap endonuclease from archaeal thermophilic organisms are typical thermostable. As used herein, the term "FEN-1" refers to a non-polymerase flap endonuclease from a eukaryote or archaeal organism. See, e.g., WO 02/070755, and Kaiser M. W., et al. (1999) J. Biol. Chem., 274:21387, which are incorporated by reference herein in their entireties for all purposes.

As used herein, the term "cleaved flap" refers to a single-stranded oligonucleotide that is a cleavage product of a flap assay.

The term "cassette," when used in reference to a flap cleavage reaction, refers to an oligonucleotide or a combination of oligonucleotides configured to generate a detectable signal in response to cleavage of a flap or probe oligonucleotide, e.g., in a primary or first cleavage structure formed in a flap cleavage assay. In preferred embodiments, the cassette hybridizes to a non-target cleavage product produced by cleavage of a flap oligonucleotide to form a second overlapping cleavage structure, such that the cassette can then be cleaved by the same enzyme, e.g., a FEN-1 endonuclease.

In some embodiments, the cassette is a single oligonucleotide comprising a hairpin portion (i.e., a region wherein one portion of the cassette oligonucleotide hybridizes to a second portion of the same oligonucleotide under reaction conditions to form a duplex). In other embodiments, a cassette comprises at least two oligonucleotides comprising complementary portions that can form a duplex under reaction conditions. In preferred embodiments, the cassette comprises a label, e.g., a fluorophore. In particularly preferred embodiments, a cassette comprises labeled moieties that produce a FRET effect.

As used herein, the term "FRET" refers to fluorescence resonance energy transfer, a process in which moieties (e.g., fluorophores) transfer energy e.g., among themselves or from a fluorophore to a non-fluorophore (e.g., a quencher molecule). In some circumstances, FRET involves an excited donor fluorophore transferring energy to a lower-energy acceptor fluorophore via a short-range (e.g., about 10 nm or less) dipole-dipole interaction. In other circumstances, FRET involves a loss of fluorescence energy from a donor and an increase in fluorescence in an acceptor fluorophore. In still other forms of FRET, energy can be exchanged from an excited donor flurophore to a non-fluorescing molecule (e.g., a "dark" quenching molecule). FRET is known to those of skill in the art and has been described (See, e.g., Stryer et al., 1978, Ann. Rev. Biochem., 47:819; Selvin, 1995, Methods Enzymol., 246:300; Orpana, 2004 Biomol Eng 21, 45-50; Olivier, 2005 Mutant Res 573, 103-110, each of which is incorporated herein by reference in its entirety).

In an exemplary flap detection assay, an invasive oligonucleotide and flap oligonucleotide are hybridized to a target nucleic acid to produce a first complex having an overlap as described above. An unpaired "flap" is included on the 5' end of the flap oligonucleotide. The first complex is a substrate for a flap endonuclease, e.g., a FEN-1 endonuclease, which cleaves the flap oligonucleotide to release the 5' flap portion. In a secondary reaction, the released 5' flap product serves as an invasive oligonucleotide on a FRET cassette to again create the structure recognized by the flap endonuclease, such that the FRET cassette is cleaved. When the fluorophore and the quencher are separated by cleavage of the FRET cassette, a detectable fluorescent signal above background fluorescence is produced.

The term "real time" as used herein in reference to detection of nucleic acid amplification or signal amplification refers to the detection or measurement of the accumulation of products or signal in the reaction while the reaction is in progress, e.g., during incubation or thermal cycling. Such detection or measurement may occur continuously, or it may occur at a plurality of discrete points during the progress of the amplification reaction, or it may be a combination. For example, in a polymerase chain reaction, detection (e.g., of fluorescence) may occur continuously during all or part of thermal cycling, or it may occur transiently, at one or more points during one or more cycles. In some embodiments, real time detection of PCR or QuARTS assay reactions is accomplished by determining a level of fluorescence at the same point (e.g., a time point in the cycle, or temperature step in the cycle) in each of a plurality of cycles, or in every cycle. Real time detection of amplification may also be referred to as detection "during" the amplification reaction.

As used herein, the term "quantitative amplification data set" refers to the data obtained during quantitative amplification of the target sample, e.g., target DNA. In the case of quantitative PCR or QuARTS assays, the quantitative amplification data set is a collection of fluorescence values obtained at during amplification, e.g., during a plurality of, or all of the thermal cycles. Data for quantitative amplification is not limited to data collected at any particular point in a reaction, and fluorescence may be measured at a discrete point in each cycle or continuously throughout each cycle.

The abbreviations "Ct" and "Cp" as used herein refer to the cycle at which a signal (e.g., a fluorescence signal) crosses a predetermined threshold value (e.g., indicative of a positive signal) for data collected during a real time PCR and/or PCR+INVADER assay. Various methods have been used to calculate the threshold that is used as a determinant of signal verses concentration, and the value is generally expressed as either the "crossing threshold" (Ct) or the "crossing point" (Cp). Either Cp values or Ct values may be used in embodiments of the methods presented herein for analysis of real-time signal for the determination of the percentage of variant and/or non-variant constituents in an assay or sample.

DETAILED DESCRIPTION OF THE INVENTION

The present invention provides molecules, e.g., synthetic DNA strands that find use as controls for monitoring processes for isolation and characterization of target nucleic acids, e.g., in stool specimens. In particular, provided herein are synthetic DNA strands configured to mimic stool sample target DNAs with respect to their characteristics and/or behavior during sample processing and results produced in DNA detection assays, e.g., to detect methylation status and/or sequence (e.g., to detect a mutation).

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

The present invention provides technology related to methods and compositions for validating the performance of assays to detect biomarkers of a disease state, e.g., cancer, e.g., colorectal cancer. In particular embodiments, the invention provides synthetic DNA fragments ("run controls") comprising sequences from the genes targeted by certain diagnostic assays for detecting colorectal cancer, e.g., NDRG4, BMP3, KRAS, and ACTB (e.g., for use as an internal (e.g., positive) control). In some embodiments, the synthetic DNA fragments have a methylation status that mimics the wild-type and/or disease-related methylation status before and/or after processing (e.g., by bisulfate reaction) to assess methylation status of biomarkers associated with a disease state, e.g., cancer, e.g., colorectal cancer. In some embodiments, the synthetic DNA fragments comprise approximately 100 to approximately 200 nucleotides or base pairs (e.g., approximately 150 nucleotides and/or base pairs) to mimic the size of DNA found in fecal samples. In some method embodiments, sense and antisense strands of each of these targets are synthesized, mixed, and annealed to form a double stranded DNA target for each gene. In some embodiments, the methylation assay genes (e.g., BMP3 and NDRG4) are provided in double-stranded forms that comprise 5-methyl cytosines (e.g., within CpG motifs) and/or are provided in double stranded unmethylated (i.e., wild-type) forms. In some embodiments related to testing for KRAS mutations, one or more of seven mutations (e.g., G34A, G34C, G34T, G35A, G35C, G35T, and/or G38A mutations) and the wild type sequence are provided. For the ACTB gene (e.g., serving as an internal control), two targets were used for each of the methylation and mutation ACTB footprints.

Some embodiments provide a run control composition comprising synthetic DNA fragments, e.g., a composition comprising synthetic gene targets for use as a control in diagnostic assays, e.g., colorectal cancer diagnostic assays. In some embodiments, the invention provides a run control comprising double stranded forms of the synthetic targets (e.g., methylated NDRG4, wild-type NDRG4, methylated BMP3, wild-type BMP3, methylation footprint ACTB, mutation footprint ACTB, seven mutants of KRAS, and/or wild type KRAS) mixed in buffer, e.g., a DNA stabilization buffer. Accordingly, some embodiments provide methods for producing a run control comprising steps such as producing double stranded forms of the synthetic targets (e.g., methylated NDRG4, wild-type NDRG4, methylated BMP3, wild-type BMP3, methylation footprint ACTB, mutation footprint ACTB, seven mutants of KRAS, and wild type KRAS, e.g., by producing single-stranded oligonucleotides and annealing them to produce double stranded forms of the synthetic targets) and mixing them, e.g., in a DNA stabilization buffer. Certain embodiments provide the mixture formulated at three concentrations of the various targets: high, low, and negative run controls with amounts that reflect the typical high, low, and negative DNA values found in stool DNA obtained from positive colorectal cancer patients.

"Target" refers to a nucleic acid or a gene (a "gene target") comprising portions, loci, regions, etc. having sequences and/or methylation status(es) that is/are to be detected or measured during a detection assay. As the DNA in stool is usually found as fragments comprising 100 to 500 bp (e.g., 100 to 250, e.g., 100 to 200, e.g., 150 bp), the regions of the nucleic acids that are to be detected or measured during a fecal sample-based assay are usually found in fragments of the targeted nucleic acids. Accordingly, as used herein, "fragment", "target fragment", or "target gene fragment" refers to a DNA of 100 to 500 bp (e.g., 100 to 250, e.g., 100 to 200, e.g., 150 bp) comprising the portions, loci, regions, etc. having sequences and/or methylation status(es) that is/are to be detected or measured during a detection assay in embodiments of the technology directed to assessing DNA of that size (e.g., a stool sample and/or fecal matter-based assay for colorectal cancer). As used in embodiments of a run control described herein, the fragments may be isolated from a natural source or the fragments may be synthetic. For instance, some embodiments provide synthetic oligonucleotides of 100 to 500 bp (e.g., 100 to 250, e.g., 100 to 200, e.g., 150 bp) comprising portions of gene targets (e.g., target fragments) that are used to calibrate, control, validate, assess, evaluate, etc. an assay for measuring and/or detecting gene targets associated with a disease state, e.g., colorectal cancer (e.g., an assay for assessing the sequence and/or methylation status of gene targets in a sample obtained from a subject who is being tested for the presence of colorectal cancer). The fragments may also be recombinant and/or semi-synthetic, e.g., comprising natural and synthesized portions.

In some embodiments, a run control fragment is complementary to or identical to an entire nucleic acid target for an assay to be evaluated by the run control, while in other embodiments, a run control fragment comprises only a portion of a target nucleic acid to be measured using the assay to be evaluated using the run control. In some embodiments, run control target fragments comprise a sequence such that amplification with primers for the target fragment sequence produces a run control amplicon that is identical in sequence to the amplicon produced from the experimental target nucleic acid.

In some embodiments, a run control target fragment comprises a sequence derived from a target nucleic acid. For example, in some embodiments, a run control fragment contains a sequence representing a target nucleic acid that has been modified, e.g., treated with bisulfate in a reaction that converts unmethylated cytosine bases to uracil bases and in which methylated cytosines are not converted. Thus, in some embodiments, control fragments for use in evaluating reactions to detect bisulfate-treated target DNA contain cytosines in place of the target's methylcytosines and thymines in place of a target's cytosines.

Run controls according to the invention are not limited to any particular number of different nucleic acid fragments and may comprise, e.g., 2, 3, 4, 5, 6, 7, 8, 9, 10, . . . 15, . . . 20, . . . 50, or more different run control nucleic acid fragments.

Although embodiments of the invention are discussed as synthetic nucleic acids, any suitable source of nucleic acid may be used in embodiments of the invention. In some embodiments, the nucleic acid is derived from a natural source (e.g., genomic DNA isolated from a cell culture, from stool, from blood cells, from a cloned source), while in some embodiments, the nucleic acid is derived from a synthetic source (e.g., synthesized by a nucleic acid synthesis apparatus known in the art (e.g., extant technology or as-yet-developed technology) and/or as provided by a commercial supplier of nucleic acids).

In some embodiments, a nucleic acid comprises a wild-type sequence and in some embodiments, a nucleic acid comprises a mutant sequence. In some embodiments, a nucleic acid comprises one or more methylated cytosines (me-C) and in some embodiments, a nucleic acid comprises one or more non-methylated cytosines (C). Preferred embodiments provide nucleic acids having defined sequences (e.g., wild-type and mutant sequences) and/or defined methylation patterns (e.g., cytosine bases within the nucleic acid are methylated or non-methylated according to a defined pattern or sequence). For example, in some embodiments, 100% of the molecules in a mixture have the same pattern of partial methylation of cytosines. In some embodiments, every cytosine within every CpG dinucleotide within a single nucleic acid molecule has a methyl group attached (e.g., 100% methylation of a nucleic acid molecule). In some embodiments related to methylated nucleic acids, each (e.g., every one) of the individual nucleic acid molecules produced according to a defined methylation pattern have the defined sequence and/or methylation pattern (e.g., 100% methylation of all nucleic acid molecules). In some embodiments related to 100% methylation of a nucleic acid molecule or of each molecule in a collection of molecules, the methylation is substantially, effectively, or essentially 100%, e.g., the sample is treated as and/or behaves as a sample having 100% methylation regardless of the actual exact state of methylation, e.g., methylation that may be less than 100% in actuality. In other embodiments, strands having different methylation patterns (e.g., 100% methylated, unmethylated, or a particular pattern of methylated and unmethylated sites) are mixed in defined amounts to produce a run control having pre-defined proportions and patterns of methylation at one or more CpG dinucleotides in a control sequence.

In preferred embodiments, the run control comprises nucleic acid that is double stranded, e.g., as provided by annealing two complementary synthetic oligonucleotides. In some embodiments, the controls are produced according to a process as follows (see, e.g., FIG. 9). DNA (e.g., single stranded DNA) is synthesized according to the sequence and methyl-C positions desired. DNA synthesis is provided by an automated DNA synthesizer and stock solutions of the four standard A, T, C, and G bases and a stock solution of 5-methyl-C. In some embodiments, single-stranded oligonucleotides are made comprising sequences from wild-type ACTB, KRAS, BMP3, and NDRG4; the KRAS 38A and KRAS 35C mutations; and methylated BMP3 and methylated NDRG4. In some embodiments, both sense and antisense (complementary) single-stranded oligonucleotides are made comprising sequences or complementary sequences from wild-type ACTB, KRAS, BMP3, and NDRG4; the KRAS 38A and KRAS 35C mutations; and methylated BMP3 and methylated NDRG4. Then, in some embodiments the single-stranded oligonucleotides are annealed (e.g., by mixing, heating (e.g., melting), and cooling, e.g., at a controlled rate, in an appropriate buffer) to provide natural-like double-stranded targets. As such, in some embodiments, annealing provides double stranded oligonucleotides comprising sequences from wild-type ACTB, KRAS, BMP3, and NDRG4; sequences from KRAS mutant 38A and KRAS mutant 35C; and from methylated BMP3 and methylated NDRG4. Then, in some embodiments, control formulations (e.g., a DNA control reagent) are produced by mixing the double stranded targets at the desired concentrations to produce the desired signal (e.g., see above) in a buffer (e.g., 80% DNA Stabilization Buffer (500 mM Tris, 150 mM EDTA, and 10 mM NaCl, pH 9) plus 50 ng/mL fish DNA). In some embodiments, controls are provided as a High, Low, and/or Negative control. Compositions and concentrations of the components for these controls are provided in Table 23, Table 24, Table 25, and/or FIG. 9.

The technology is not limited in the buffer that finds use to produce the control. For example, the buffer may be HEPES, PIPES, SSC, MES, MOPS, phosphate buffer, citric acid (citrate) based buffers, other Tris buffers, etc. and may have any suitable pH (typically from 5.5 to 10).

In some embodiments, the run control comprises nucleic acid that is derived from a plasmid. For example, in some embodiments, run control fragments are cloned into a plasmid vector. In some embodiments, the vector comprises the sequence of a plasmid vector (e.g., a pUC plasmid, etc.) and one or more run control fragments, e.g., linked in series (e.g., directly or separated by linkers) and separated by restriction sites, e.g., as described in Application Ser. No. 61/899,302, which is incorporated herein by reference.

In some embodiments, run control fragments are used to evaluate, calibrate, assess, and/or validate assays for the identification, detection, and/or characterization of disease, a pre-disease state, or susceptibility to disease in a subject (e.g., human). In certain embodiments, the run control fragments correspond to target sequences encompassing disease biomarkers (e.g., cancer biomarkers). In some embodiments, run control fragments and target sequences each comprise at least one locus that is indicative of a disease or predisposition to a disease (e.g., cancer, such as colorectal cancer, etc.). In some embodiments, a biomarker for disease comprises a mutation (e.g., a point mutation, deletion, insertion) at a locus in a subject, while in some embodiments a biomarker consists of a particular methylation state at a locus in a subject. In some embodiments, a biomarker is the ratio of mutated to un-mutated or methylated to unmethylated nucleic acids at a particular locus in a sample or subject. In some embodiments, a diagnostic marker is related to the quantity of a target nucleic acid present in a sample, e.g., the amount of certain DNA in a stool sample from a subject. Nucleic acids in the run control mimic, in various embodiments, the sequence of a nucleic acid from a healthy (wild-type) subject, the sequence of a nucleic acid from a subject having a disease (e.g., a mutant sequence), the methylation state of a nucleic acid from a healthy (wild-type) subject, the methylation state of a nucleic acid from a subject having a disease, the sequence that a nucleic acid from a healthy (wild-type) subject is expected to have after treatment with bisulfite, and/or the sequence that a nucleic acid from a subject having a disease is expected to have after treatment with bisulfite.

In certain embodiments, analysis of biomarkers comprises analysis of mutations in the KRAS gene and/or analysis of the methylation states of specific loci in BMP3 and/or NDRG4, and the run controls comprise fragments containing the corresponding loci. In preferred embodiments, the run controls further comprise a sequence of a reference gene, e.g., beta actin (ACTB), for use, e.g., as a control (e.g., an internal control) for an assay (e.g., a positive control).

In particular embodiments, a run control for a colorectal cancer mutation biomarker assay comprises two or more run control fragments corresponding to (e.g., identical to, substantially identical to, complementary to, or substantially complementary to) target sequences encompassing loci that are indicative of cancer or pre-cancer when a particular mutation is present. In some embodiments, a run control comprises target sequences encompassing loci that are indicative of cancer or pre-cancer when methylated or unmethylated. Exemplary run control fragments comprise the sequences provided in FIG. 6. Modifications to and variations of such sequences and methylation patterns are within the scope of the present invention (e.g., comprising different sequences to reflect other alleles, mutants, and/or methylation patterns; different amounts of methylation (e.g., less than 100%, e.g., 90%, 80%, 70%, 60%, 50%, 40%, 30%, 20%, 10% methylation); different combinations of run control fragments corresponding to difference target sequences (e.g., different cancer biomarkers), etc.)

In some embodiments, synthetic DNA is produced (e.g., for methylation and/or mutation assays) by synthesis on a nucleic acid synthesis apparatus. In some embodiments, synthetic DNA is produced using solid-phase synthesis and phosphoramidite monomers derived from protected 2'-deoxynucleosides (dA, dC, dG, and dT) (e.g., 3'-O—(N,N-diisopropyl phosphoramidite) derivatives of the standard nucleosides (nucleoside phosphoramidites)) and chemically modified nucleosides such as 5-methyl-dC. In some embodiments, synthetic DNA is purified by HPLC.

In some embodiments, the run control comprises synthetic DNA fragments and a buffer. For example, in some embodiments, the run control comprises DNA Stabilization Buffer (500 mM Tris, 150 mM EDTA, and 10 mM NaCl, pH 9), e.g., 50% to 100% (e.g., 55%, 60%, 65%, 70%, 75%, 80%, 85%, 90%, 95% DNA Stabilization Buffer) and fish DNA (e.g., fish (e.g., salmon) sperm DNA, e.g., at 10 to 100 ng/mL, e.g., 20 to 80 ng/mL, e.g., 30 to 60 ng/mL, e.g., 50 ng/mL). The technology is not limited to the use of fish DNA, but any source of background DNA may be used that is suitable for the technology (e.g., calf thymus DNA, tRNA, synthetic random DNA, bacterial genomic DNA, etc.).

In some embodiments, the synthetic nucleic acids are present in an amount of from approximately 0 (zero) to approximately $10^6$ (e.g., 1E+6) copies/mL. For example, in some exemplary embodiments, the synthetic nucleic acids are present in the following amounts in a "High" control: 2.0E+05 copies/mL PCTRL-ACTB-WT-ds, 5.0E+04 copies/mL PCTRL-KRAS-WT-ds, 5.0E+04 copies/mL PCTRL-126-NDRG4-WT-ds, 5.0E+04 copies/mL PCTRL-126-BMP3-WT-ds, 2.8E+03 copies/mL PCTRL-KRAS-38A-ds, 5.8E+03 copies/mL PCTRL-KRAS-35C-ds, 1.4E+04 copies/mL PCTRL-126-NDRG4-ME-ds, and 5.5E+03 copies/mL PCTRL-126-BMP3-ME-ds. In some embodiment, the synthetic nucleic acids are present in the following amounts in a "Low" control: 2.0E+05 copies/mL PCTRL-ACTB-WT-ds, 5.0E+04 copies/mL PCTRL-KRAS-WT-ds, 5.0E+04 copies/mL PCTRL-126-NDRG4-WT-ds, 5.0E+04 copies/mL PCTRL-126-BMP3-WT-ds, 1.0E+03 copies/mL PCTRL-KRAS-38A-ds, 2.5E+03 copies/mL PCTRL-KRAS-35C-ds, 6.0E+03 copies/mL PCTRL-126-NDRG4-ME-ds, and 2.2E+03 copies/mL PCTRL-126-BMP3-ME-ds. In some embodiments, the synthetic nucleic acids are present in the following amounts in a "Negative" control: 6.6E+04 copies/mL PCTRL-ACTB-WT-ds, 1.7E+04 copies/mL PCTRL-KRAS-WT-ds, 1.7E+04 copies/mL PCTRL-126-NDRG4-WT-ds, and 1.7E+04 copies/mL PCTRL-126-BMP3-WT-ds.

In some embodiments, run controls are provided in multiples of the concentrations used in the control reactions, e.g., to provide a concentrated stock solution (e.g., 2×, 3×, 4×, 5×, 10×, 20×, 25×, 50×, 100×, 1000×) of a run control that is diluted (e.g., with a buffer) before use.

In some embodiments, an exemplary assay utilizing a run control of the present invention proceeds as follows. Nucleic acid is isolated from a biological or environmental source (e.g., a stool sample). In some embodiments, the nucleic acid is processed with a capture reagent (e.g., a capture probe) to concentrate, isolate, and/or purify the nucleic acid from non-target nucleic acids and non-nucleic acid substances. In some embodiments, the run control composition is also processed in parallel with the capture reagent. In some embodiments, the sample and/or the nucleic acid isolated from the biological or environmental source (e.g., a stool sample) is treated with an inhibitor removal reagent, either before or after capture with the capture reagent. In some embodiments, the run control composition is also processed in parallel with the inhibitor removal reagent.

In some embodiments, the nucleic acid is treated with a bisulfite reagent to convert non-methylated cytosines to uracils. In some embodiments, the run control composition is also processed in parallel with a bisulfite reagent to convert non-methylated cytosines to uracils. In some embodiments, the run control composition comprises synthetic nucleic acids that have a methylation status that is the methylation status known to be associated with a disease state. In some embodiments, the run control composition comprises synthetic nucleic acids that have a sequence that is the sequence expected when a methylation state associated with a disease state is processed with a bisulfite reagent to convert non-methylated cytosines to uracils.

In some embodiments, the nucleic acid is assayed, e.g., by a QuARTS assay. In some embodiments, the run control composition is also processed and assayed in parallel with the nucleic acid from the sample. The run control and the isolated nucleic acid are subject to the same reaction and assay conditions (e.g., amplification conditions), and the results of the reactions are detected, e.g., in real time, for both the target and run control. Then, the results of the assay with the run control are assessed relative to the expected results for the run control (e.g., to determine if the run control results are within a pre-defined acceptable range) to provide an indicator that the assay testing the nucleic acid from the patient sample is valid or is not valid, to assess assay performance, user error, instrumentation errors, reagent quality, etc.

Processing the run controls in the same manner as the test sample (e.g., the nucleic acid from the biological, environmental, etc. sample) provides for assessing the performance of the procedures and assays on the test sample and thus provides information about the validity and/or confidence in the assay results.

In certain embodiments, the nucleic acid isolated from the patient sample and/or the run controls are added to a reaction mixture (reaction mix), e.g., for PCR and/or QuARTs assay. Typically, these reaction mixtures contain reagents for polymerase chain reaction (PCR) amplification, although reaction mixtures for other methods of amplification and/or analysis are within the scope of the present invention. In some embodiments, reaction mixtures comprise PCR reagents for amplifying a nucleic acid target sequence. The reaction mixtures employed in the method may therefore comprise: one or more pairs of primers, a suitable PCR buffer (e.g., pH buffered, comprising salt (e.g., KCl) and a source of divalent cation (e.g., $MgCl_2$), etc.), deoxynucleoside triphosphates (e.g., dGTP, dATP, dTTP, and dCTP), and a thermostable DNA polymerase. Depending on the application, the reaction mixture may also comprise additional components for further analysis, manipulation, and/or detection of polynucleotides or target sequences therein, e.g., invasive oligonucleotide(s), flap oligonucleotide(s), flap endonuclease (e.g., thermostable FEN-1), FRET cassette(s), etc.

The exact identities and concentrations of the reagents present in the reaction mixture may be similar to or the same as those employed in the field. In some embodiments, a reaction mixture contains $Mg^{2+}$ at a concentration of between about 1.8 mM and 3 mM, 4 mM to 10 mM, 6 mM to 9 mM, etc. Exemplary reaction buffers and DNA polymerases that may be employed in the subject reaction mixture include those described in various publications (e.g., Ausubel, et al., Short Protocols in Molecular Biology, 3rd ed., Wiley & Sons 1995; Sambrook et al., Molecular Cloning: A Laboratory Manual, Third Edition, 2001 Cold Spring Harbor, N.Y.; herein incorporated by reference in their entireties). Reaction buffers and DNA polymerases suitable for PCR may be purchased from a variety of suppliers, e.g., Invitrogen (Carlsbad, Calif.), Qiagen (Valencia, Calif.), and Stratagene (La Jolla, Calif.). Exemplary polymerases include Taq, Pfu, Pwo, UlTma, and Vent, and variants thereof, although many other polymerases may be employed in certain embodiments. Exemplary flap endonucleases include Afu FEN-1, Pfu FEN-1 and Ave FEN-1 (See, e.g., WO 02/070755, and Kaiser M. W., et al. (1999) J. Biol. Chem., 274:21387).

Guidance for the reaction components suitable for use with a polymerase and suitable conditions for their use is found in the literature supplied with the polymerase. Primer design is described in a variety of publications (e.g., Diffenbach and Dveksler, PCR Primer, A Laboratory Manual, Cold Spring Harbor Press 1995; R. Rapley, The Nucleic Acid Protocols Handbook (2000), Humana Press, Totowa, N.J.; Schena and Kwok et al., Nucl. Acid Res. 1990 18:999-1005; herein incorporated by reference in their entireties). Primer and probe design software programs are also commercially available, including without limitation, Primer Detective (ClonTech, Palo Alto, Calif.), Lasergene, (DNASTAR, Inc., Madison, Wis.), OLIGO (National Biosciences, Inc., Plymouth, Minn.), and iOligo (Caesar Software, Portsmouth, N.H.).

In particular embodiments, a reaction mix contains reagents for assaying multiple different target sequences in parallel (e.g., at least 2, 3, 4 . . . 10, or more). In these cases, the reaction mix may contain multiple pairs of PCR primers. In certain embodiments, the various oligonucleotides used in the method are designed so as not to interfere with one another. In a multiplex reaction, the primers may be designed to have similar thermodynamic properties (e.g., similar $T_{mS}$, G/C content, hairpin stability, and in certain embodiments may all be of a similar length (e.g., from 18 to 30 nt (e.g., 20 to 25 nt). In some embodiments, other reagents used in the reaction mixture are $T_m$ matched, to work under the same temperature(s) as other components, or during a selected subset of temperatures used, e.g., during a thermocycling reaction.

In some embodiments, the reaction mixture is present in a vessel, including without limitation, a tube; a multi-well plate (e.g., 96-well, 384-well, 1536-well), a microfluidic device, etc. In certain embodiments, multiple multiplex reactions are performed in the same reaction vessel. Depending on how the reaction is performed, the reaction mixture may be of any volume, e.g., 0.1 μl to 5 μl, 5 μl to 200 μl (e.g., 10 μl to 100 μl), although volumes outside of this range are envisioned.

In certain embodiments, a reaction mix comprises a nucleic acid (e.g., comprising a target sequence, from a biological sample, from an environmental sample, synthetic (e.g., from a run control), etc.). In particular embodiments, the mix comprises genomic DNA, fragments thereof, or an amplified version thereof (e.g., genomic DNA amplified using the methods of Lage et al, Genome Res. 2003 13: 294-307 or published patent application US 2004/0241658 both of which are herein incorporated by reference in their entireties), e.g., from a patient to be tested for a disease, e.g., colorectal cancer. In exemplary embodiments, the genomic sample may contain genomic DNA from a mammalian cell such a human, mouse, rat or monkey cell. The sample may be made from cultured cells or cells of a clinical sample (e.g., a tissue biopsy, scrape or lavage or cells of a forensic sample (i.e., cells of a sample collected at a crime scene), etc.).

In particular embodiments, a nucleic acid in a reaction mix is obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, cerebrospinal fluid, synovial fluid, urine, amniotic fluid, and semen. In particular embodiments, a sample may be obtained from a subject (e.g., a human) and it may be processed prior to use in the subject assay. For example, the nucleic acid may be extracted from the sample prior to use, methods for which are known. In some embodiments, nucleic acid is extracted, isolated, purified, removed from stool (e.g., human stool, a stool sample, etc.). For example, nucleic acid (e.g., DNA) can be extracted from stool from any number of different methods, including those described in, e.g., Coll et al. J. Clinical Microbiology 1989 27: 2245-2248; Sidransky et al. Science 1992 256: 102-105; Villa, Gastroenterology 1996 110: 1346-1353; Nollau, BioTechniques 1996 20: 784-788; U.S. Pat. Nos. 5,463,782; 7,005,266; 6,303,304; 5,741,650; herein incorporated by reference in their entireties. Commercial DNA extraction kits for the extraction of DNA from stool include the QiAamp stool mini kit (QIAGEN, Haden, Germany), Instagene Matrix (Bio-Rad, Hercules, Calif.), and RapidPrep Micro Genomic DNA isolation kit (Pharmacia Biotech Inc., Piscataway, N.J.), among others. In preferred embodiments, DNA is extracted from stool samples as described, e.g., in U.S. Patent Publication 2012/0288868, incorporated herein by reference in its entirety for all purposes. In some embodiments the DNA is treated with bisulfate prior to use in an assay, wherein unmethylated cytosine bases are converted to uracil bases.

In certain embodiments, a reaction mixture (e.g., comprising a nucleic acid from the patient; comprising a run control) comprises one or more reagents (e.g., oligonucleotides such as primers, flap probes, detection cassettes; enzymes such as polymerases; chemical reagents; etc.) for performing amplification, processing, manipulation, analysis, detection steps or assays (e.g., other than and/or in addition to PCR). The present invention is not limited by the scope of the nucleic acid analysis, manipulation, and/or detection methods with which it finds use.

In some embodiments, multiple different reaction mixes (e.g., at least one comprising a run control and at least one comprising a nucleic acid from a patient sample) are provided (e.g., for use in an experiment or assay). In some embodiments, multiple vessels (e.g., wells, tubes, channels, etc.) are provided, each containing a reaction mix (e.g., at least one comprising a run control and at least one comprising an experimental target nucleic acid).

In certain embodiments, the run control compositions, reaction mixtures, and/or methods described herein find use in a variety of diagnostic, medical, analytical, and research applications, and the invention should not be viewed as limited to any particular field or use. However, in particular embodiments, the present invention finds use in the analysis, detection, characterization, etc. of nucleic acid (e.g., human nucleic acid, target nucleic acid, etc.) from stool. Compositions, methods, devices, etc. for use the embodiments described herein are found in, for example, U.S. Pat. Nos. 8,361,720; 7,981,612; 7,368,233; 6,964,846; 6,919,174; 6,849,403; 6,844,155; 6,818,404; 6,750,020; 6,586,177; 6,551,777; 6,503,718; 6,498,012; 6,482,595; 6,475,738; 6,428,964; 6,415,455; 6,406,857; 6,351,857; 6,303,304; 6,300,077; 6,280,947; 6,268,136; 6,203,993; 6,146,828; 6,143,529; 6,020,137; 5,952,178; 5,928,870; 5,888,778; 5,830,665; 5,741,650; 5,670,325; each of which is herein incorporated by reference in its entirety for any purpose. In certain embodiments, the compositions and methods described herein find use in, for example, a quantitative allele-specific real-time target and signal amplification assay (QUARTS assay), such as the ones described in Zou et al. Clinical Chemistry, February 2012 vol. 58(2): 375-383; herein incorporated by reference in its entirety.

In some embodiments, compositions and methods are employed in assays to detect an oncogenic mutation (which may be a somatic mutation) in, e.g., PIK3CA, NRAS, KRAS, JAK2, HRAS, FGFR3, FGFR1, EGFR, CDK4, BRAF, RET, PGDFRA, KIT, or ERBB2, which mutation may be associated with breast cancer, melanoma, renal cancer, endometrial cancer, ovarian cancer, pancreatic cancer, leukemia, colorectal cancer, prostate cancer, mesothelioma, glioma, meullobastoma, polythemia, lymphoma, sarcoma or multiple myeloma (see, e.g., Chial 2008 Proto-oncogenes to oncogenes to cancer. Nature Education 1:1). In some embodiments, compositions and methods are employed in assays to detect the methylation status of a nucleic acid (e.g., a gene), e.g., NDRG4, BMP3, that is associated with a disease, e.g., a cancer such as colorectal cancer.

EXPERIMENTAL

During the development of embodiments of technology related to tests for colorectal cancer, experiments suggested that including control DNA samples would provide an improved test. Accordingly, technologies are provided herein comprising DNA controls that generate specific signals when processed through a workflow in parallel with experimental (e.g., unknown) samples (e.g., from a patient). In particular, the controls provided herein comprise various nucleic acid targets that are captured during the capture process, converted during the bisulfite conversion, and present the correct sequence for detection by the QuARTS mutation and/or methylation assays.

Experiments were conducted to develop controls for use in an assay to test for colorectal cancer. The development of control DNA samples was guided by certain design principles and characteristics that are desirable for such a control. In particular, a useful set of controls comprises amounts of the diagnostic biomarkers that reflect typical high, low, and negative DNA values found in stool DNA obtained from positive colorectal cancer patients. Additionally, useful controls are supplied at an aliquot volume that matches an actual sample volume or that is supplied as a concentrated stock with dilution buffer for preparation of the proper volume prior to use and are designed to indicate if the processing of a test sample (e.g., DNA isolation, methyl conversion, and purification) was completed successfully. Furthermore, useful controls contain targets to generate signal for each fluorescent dye in the methylation and mutation assays. Useful controls are designed to provide an adequate signal in assays (e.g., the QUARTS assay) if +/−10% of recommended control volume is utilized and processed correctly and have a failure rate≤1% when processed according to instructions for use. Finally, useful controls are packaged to prevent the controls from being used incorrectly by a user (e.g., through identification by different color caps, barcoding, or other marking options). These principles are to be understood as providing general guidance in the development of the technology and do not limit the technology provided herein.

During the development of various embodiments of the invention described herein, DNA controls were tested that contained combinations of the biomarkers NDRG4, BMP3, KRAS, and ACTB. In some embodiments, controls comprised each of the methylation assay genes (BMP3 and NDRG4) in methylated (e.g., comprising 5-methyl cytosines at CpG motifs) and unmethylated (e.g., wild type) forms. Some embodiments of the controls comprised one or more mutant KRAS (e.g., G34A, G34C, G34T, G35A, G35C, G35T, and G38A) and/or the wild type sequence. For the ACTB gene, two targets were used for each of the methylation and mutation ACTB footprints.

During the development of controls comprising these biomarkers, experiments were conducted to test nucleic acids from different sources for use as controls. In particular, data were collected from experiments to compare the use of genomic DNA, plasmids, and synthetic DNA as control samples for colorectal cancer diagnostics. The data collected showed that synthetic DNA provided advantages relative to the genomic and plasmid DNA.

Definitions and Acronyms

The following definitions and acronyms are used herein: ACTB refers to the gene encoding β-actin, which is used as a reference gene for QuARTS assays; BMP3 refers to the gene encoding bone morphogenetic protein 3; bp refers to a base pair of double-stranded DNA; gDNA refers to genomic DNA; KRAS refers to the Kirsten rat sarcoma viral oncogene homolog (V-Ki-ras2); NDRG4 refers to N-myc downstream regulated gene 4; and nt refers to nucleotide base of a nucleic acid such as a DNA. "Zymo" refers to Zymo Research, Irvine Calif.

Example 1—Genomic DNA

During the development of embodiments of the invention described herein, genomic DNA was tested for use as a control sample to be included in assays for evaluating biomarkers of colorectal cancer. Several sources of genomic DNA were considered including cell line derived genomic DNA, DNA purified from peripheral blood mononuclear cells (PBMCs), and genomic DNA isolated from stool (sDNA).

gDNA from Cell Lines

It was contemplated that genomic DNA derived from cell lines may provide a control material with desirable characteristics because cell lines exist that have DNA comprising KRAS mutations, cell lines exist that have DNA comprising methylated markers, and cell lines are easily stored in a frozen state. Accordingly, experiments were conducted to test the use of genomic DNA as a control.

Testing Production of Run Controls Having Defined Representation of Methylated Loci It was contemplated to use a blending strategy for production of the control DNA (Table 1). To provide a control DNA sample comprising the desired methylation and mutation markers, genomic DNA from three different cell lines would be mixed to provide a DNA control composition for testing (Table 1). In particular, the control DNA formulations would comprise gDNA from a mutation-negative, methylation-negative cell line spiked with an appropriate level of gDNA from cell lines having the relevant target sequences (e.g., methylated targets and two KRAS mutation targets).

TABLE 1

| Target blending strategy for cell line gDNA based DNA controls | | | | | | |
|---|---|---|---|---|---|---|
| | gDNA Description | | | DNA Control Composition | | |
| gDNA Source | % methylation status | KRAS 38A | KRAS 35C | DNA Control 1, High | DNA Control 2, Low | DNA Control 3, Negative |
| cell line 1 | 0% | − | − | 80% | 96% | 100% |
| cell line 2 | 50% | + | − | 10% | 2% | 0% |
| cell line 3 | 50% | − | + | 10% | 2% | 0% |

To test genomic DNA to use for mixing as a control, genomic DNA prepared from the cell lines HCT-116 (Zymo), HTB-38D (ATCC), and HTB-72D (ATCC) was obtained from commercial suppliers and tested. The HCT-116 methylated DNA is genomic DNA isolated from cell line HCT-116 by the commercial supplier (Zymo) and then methylated in vitro by the commercial supplier. To assess the methylation status of the commercial gDNA preparations, the biomarkers Vimentin, TFPI2, BMP3 and NDRG4 DNA were screened for methylation status (Table 2). The results indicated that the methylation status was not as predicted for all markers. For example, TFPI2 was detected as methylated in the "unmethylated" DNA control (Table 2). This is consistent with the known instability of methylation status in cell line DNAs (see, e.g., Grafodatskaya et al. (2010) "EBV transformation and cell culturing destabilizes DNA methylation in human lymphoblastoid cell lines" Genomics 95: 73-83; Saferali et al. (2010) "Cell culture-induced aberrant methylation of the imprinted IG DMR in human lymphoblastoid cell lines" Epigenetics 5(1): 50-60; Sugawara et al. (2011) "Comprehensive DNA methylation analysis of human peripheral blood leukocytes and lymphoblastoid cell lines" Landes Bioscience 6(4): 508-515).

TABLE 2

| Methylated Status in Cell Line gDNA | | | | |
|---|---|---|---|---|
| Description | Vimentin | TFPI2 | BMP3 | NDRG4 |
| Methylated gDNA Control from HCT-116 (Zymo) | + | + | + | + |
| Unmethylated gDNA Control from HCT-116 (Zymo) | − | + | − | − |
| HTB-38D (ATCC) | + | + | + | + |
| HTB-72D (ATCC) | − | − | − | − |

In further experiments, genomic DNA was needle-sheared and processed through the bisulfite conversion reaction in bulk, aliquoted, and assayed by the QUARTS assay method. The material did not go through the capture process. Based on what was known about the input control material (e.g., information from the supplier and data obtained in the experiments discussed above), it was expected that the strands detected would be similar for each marker and that % methylation would be 100%. Percent (%) methylation is determined by dividing the number of methylation target strands detected by the number of ACTB (internal control, unmethylated) strands detected. However, the results indicated that the mean strands detected and values for mean % methylation from 97 compiled runs were substantially less than the 100% value that was predicted (Table 3).

TABLE 3

| Methylation Status of Methylated Control | | | | |
|---|---|---|---|---|
| Methylation Assay Used for Evaluation | Marker | Mean Strands Detected in QuARTS Methylation Assays | % Methylation | CV - mean strands detected (n = 97 runs) |
| ACTB/TFPI2/BMP3 | ACTB | 13,105 | NA | 11% |
| | TFPI2 | 5,326 | 41% | 18% |
| | BMP3 | 4,705 | 36% | 9% |
| ACTB/NDRG4/ Vimentin | ACTB | 12,816 | NA | 9% |
| | NDRG4 | 5,961 | 47% | 8% |
| | Vimentin | 3,893 | 30% | 14% |

Accordingly, experiments were performed to improve the amount of methylated DNA in the genomic DNA materials obtained from the commercial suppliers. Experiments were performed to investigate increasing the methylation % using in vitro methylation of the genomic DNA from HCT-1116 cells. Surprisingly, data collected during these experiments indicated that the efforts were not successful at increasing the % methylation of the targets relative to the methylated material obtained from the commercial supplier, which was not subjected to further methylation in vitro (Table 4).

TABLE 4

In Vitro Methylation Optimization Results

| Sample Description | Strands Recovered | | | | | |
|---|---|---|---|---|---|---|
| | ACTB (ANV) | NDRG4 Strands (% methylation) | Vimentin Strands (% methylation) | ACTB (ATB) | TFPI2 Strands (% methylation) | BMP3 Strands (% methylation) |
| Unmethylated HCT-1116 gDNA | 18,596 | 0 | 0 | 27,804 | 500 | 0 |
| In vitro Methylated HCT-116 gDNA | 12,993 | 6,151 (47%) | 4,996 (38%) | 20,523 | 10,672 (52%) | 9,066 (44%) |
| Methylation Control (Zymo, Cat No. D5014) | 26,709 | 12,979 (49%) | 9,241 (35%) | 35,762 | 15,724 (44%) | 15,340 (43%) |

Testing Production of Run Controls Having Defined Representation of Mutation Loci In addition to methylation controls, the control DNA mixture comprises mutant and wild-type gene sequences, e.g., KRAS mutant and wild-type sequences. Accordingly, to provide KRAS mutation targets, cell lines containing KRAS mutations were identified using information from the Sanger Institute Cancer Genome Project (Table 5). Table 5 summarizes the characterization of cell lines containing KRAS mutations according to information provided by ATCC.

TABLE 5

Cell lines containing KRAS mutations

| Mutation | Cell Line | ECACC PN | ploidy[a] |
|---|---|---|---|
| KRAS 34G > A | A549 | 86012804 | This is a hypotriploid human cell line with the modal chromosome number of 66, occurring in 24% of cells. Cells with 64 (22%), 65, and 67 chromosome counts also occurred at relatively high frequencies; the rate with higher ploidies was low at 0.4%. There were 6 markers present in single copies in all cells. They include der(6)t(1; 6) (q11; q27); ?del(6) (p23); del(11) (q21), del(2) (q11), M4 and M5. Most cells had two X and two Y chromosomes. However, one or both Y chromosomes were lost in 40% of 50 cells analyzed. Chromosomes N2 and N6 had single copies per cell; and N12 and N17 usually had 4 copies. |
| KRAS 34G > T | UM-UC-3 | 96020936 | This is a hypertriploid human cell line. The modal chromosome number was 80, occurring in 42% of cells. Cells with 78 chromosomes also occurred at a high frequency. The rate of cells with higher ploidies was 2.5%. There were 30 or more marker chromosomes in each cell. They included der(1)t(1; ?) (p32; ?), ?t(1p5p), i(3q), t(7q14q), ?t(2p3p) and others. The X and N3 had single copy per cell, and others were generally two to three copies per cell. |
| KRAS 34G > C | HuP-T3 | 93121055 | no information on cytology from ATCC[b] |
| KRAS 35G > A | LS-174T | 87060401 | Cytogenetic Analysis: 45, X; one X chromosome missing; no other chromosomal aberrations |
| KRAS 35G > T | SHP-77 | 98110201 | no information on cytology |
| KRAS 35G > C | RPMI-8226 | 87012702 | Cytogenetic Analysis: Unstable karyotype in triploid range of 68-70 chromosomes. Two large marker chromosomes with terminal centromeres. |

TABLE 5-continued

| Cell lines containing KRAS mutations | | | |
|---|---|---|---|
| Mutation | Cell Line | ECACC PN | ploidy[a] |
| KRAS 38A | HCT-116 | NA | Cytogenetic Analysis: The stemline chromosome number is near diploid with the modal number at 45 (62%) and polyploids occurring at 6.8%. The markers 10q+ and t(?8p; 18q) are present in all metaphases and t(9q; ?16p−), in 80% of the cells karyotyped. N16 is monosomic in the presence of, but disomic in the absence of t(9q; ?16p−). N10 and N18 are monosomic and other chromosomes from those mentioned above are disomic. Q-band observations revealed the presence of the Y chromosome, but not in all cells (50% of cells lacked the Y in G-band karyotypes). |

a. These cell line ploidy levels are not confirmed and chromosomal aberrations are common in cell lines. Reliable assignment of gene copy numbers in cell line DNA is therefore difficult.

b. Information for the HuP T3 cell line reported in the German Collection of Microorganisms and Cell Cultures (DSMZ, Braunschweig) is as follows:

Cytogenetics 1: flat-moded hypodiploid karyotype with 13% polyploidy; 39(36-40)<2n>XY, −6, −8, −9, −10, −12, −13, −17, −17, −19, −20, +3 mar (2 rings), del(4)(p15), add(11)(q22.3; HSR), add(12)(q24; HSR), add(19)(p13), add(21)(p12); gene amplification suggested by large HSR; ch 17 nullisomy DNA fingerprinting (unique DNA profile with (gtg) 5 multilocus probe)

immunological analysis (cytokeratin+(100%), desmin−, endothel−, GFAP−, neurofilament−, vimentin+)

isoenzymes (confirmed as human with IEF of AST, NP)

reverse transcriptase (reverse transcriptase not detected).

Experiments were performed to verify the presence of four KRAS mutations in cell line-derived gDNA verified using the mutation detection assay. However, recoveries (apparent number of strands based on signal from the detection assay) from these experiments did not align with expected numbers of strands based on copy number input measured by OD 260 (Table 6). It is contemplated that the cause of this discrepancy is the abnormal ploidies in the cell lines.

TABLE 6

| KRAS Mutations Present in Cell Line gDNA | | | | | |
|---|---|---|---|---|---|
| Cell line Source | KRAS mutation | Input strands | Strands Recovered | % recovery of input | N |
| UM-UC-3 | 34T | 20000 | 71034 | 355% | 2 |
| HCT-116 | 38A | 20000 | 43843 | 219% | 2 |
| HuP-T3 | 34C | 20000 | 5034 | 25% | 2 |
| A549 | 34A | 20000 | 41502 | 208% | 2 |

Testing Production of Short DNA Strands

The molecular weight of DNA in stool is typically low, e.g., around 100 to 1000 bp (see, e.g., Diehl et al. (2008) "Analysis of Mutations in DNA Isolated From Plasma and Stool of Colorectal Cancer Patients" Gastroenterology 135: 489-498). Accordingly, to provide DNA controls that mimic the performance of stool samples, the control DNA should have a low molecular weight, e.g., in the range of approximately 150 bp to 1000 bp. Because cell line gDNA has a higher molecular weight than desired for the controls, experiments were conducted to characterize gDNA that is sheared prior to use in DNA control manufacture. Two methods of shearing were evaluated as described below:

1) Needle shearing—gDNA was passed through a 26 ½ gauge needle 10 times. This method is commonly used to fragment intact gDNA; and 2) Covaris S2 sonication—gDNA was sonicated using the Covaris S2 set at 150 bp and 200 bp median fragment size. This method of DNA shearing is commonly used to prepare DNA for CHiP analysis.

Figure 1B:
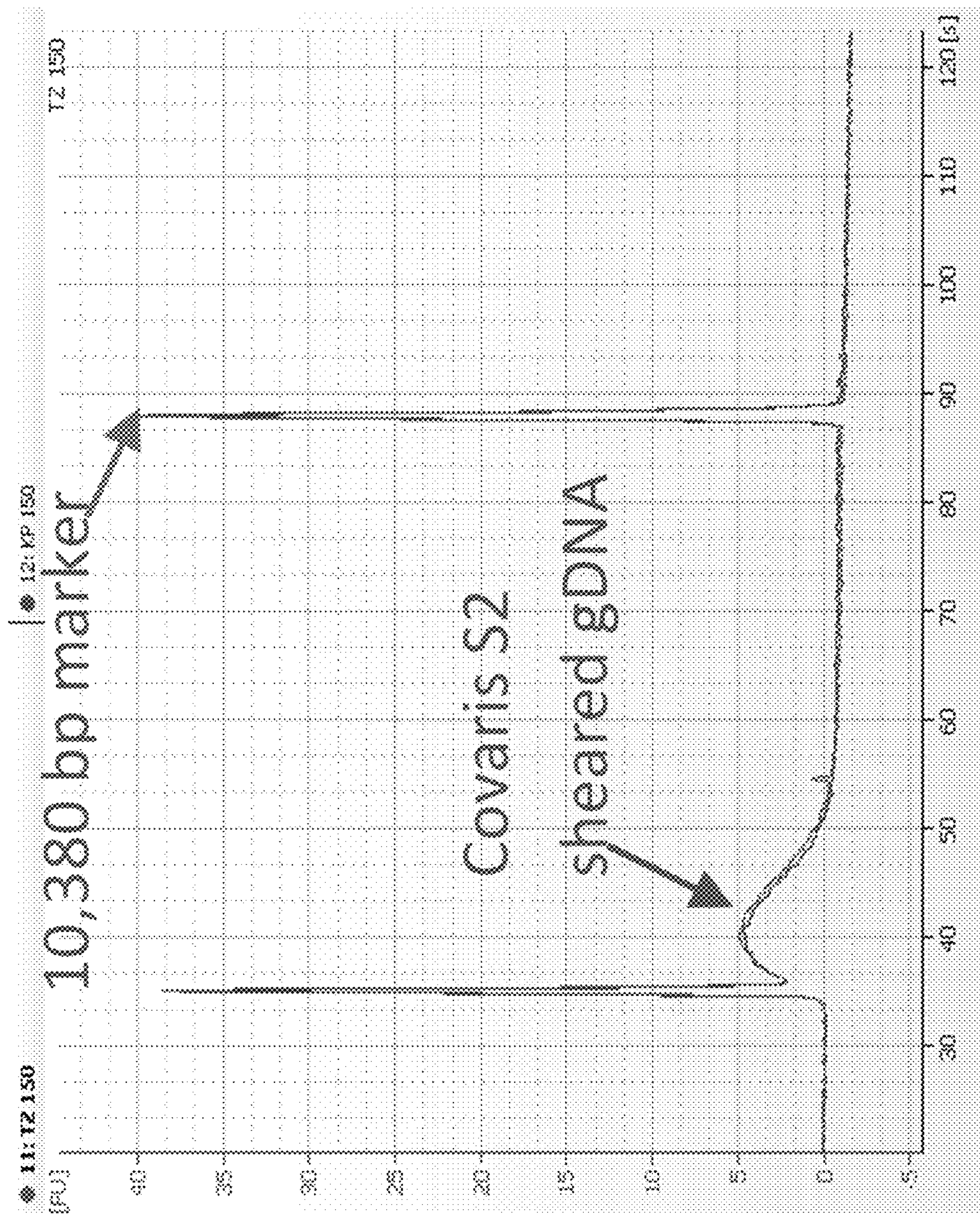

Sheared gDNA was analyzed on a Bioanalyzer. The needle shearing method resulted in nucleic acids >10,000 bp in length while the Covaris S2 was able to shear the intact genomic DNA into fragments of approximately 50 bp to 300 bp (FIG. 1). Sheared gDNA was processed through the capture, bisulfate conversion, and QuARTS methylation reactions to detect ACTB. The strand recovery data collected show greater recovery from Covaris S2 sheared gDNA than from needle sheared gDNA (Table 7), indicating that smaller nucleic acid fragments are favored in the DNA isolation process and in QuARTS assay detection.

TABLE 7

| Comparison of Shearing Processes | | | | |
|---|---|---|---|---|
| Shearing Method | Number of Samples Tested | Mean (% Recovery ACTB) | Min (% Recovery ACTB) | Max (% Recovery ACTB) |
| Covaris | 36 | 15.6% | 5% | 23% |
| needle | 24 | 3.7% | 1% | 8% |

The data collected indicate that the length of the DNA fragments affects capture recovery and QuARTS assay recovery differently. In particular, a decreased fragment length increases recovery in the capture process but decreases recovery in the QUARTS assay reaction due to loss (fragmentation or damage) of the QUARTS assay footprint.

In sum, the experiments evaluating cell line-derived genomic DNA as a source of DNA for assay controls indicated that cell line-derived gDNA is not feasible for the manufacture of the needed DNA Controls. The materials and processes required to formulate DNA controls that meet the design principles using cell line-derived gDNA are variable and inefficient.

Specifically, the experiments indicated that cell line-derived gDNA is not consistently or completely methylated, cell line-derived gDNA has inconsistent copy numbers, and cell line-derived gDNA cannot be characterized for methylation status and gene copy numbers. Furthermore, in vitro methylation is an inefficient and uncontrolled process that is not suitable for manufacturing. To meet the safety and performance requirements for colorectal cancer screening assays, reagents must be reproducible from lot to lot. Therefore, the use of gDNA from cell lines was considered not viable.

Commercial PBMC gDNA

Next, purified genomic DNA from PBMCs was assessed as an alternative source of genomic DNA. This type of genomic DNA is available from a number of commercial suppliers (e.g., EMD Millipore, Cat No. 69237-3). As discussed above, the DNA in stool has a low molecular weight (e.g., approximately 150 to 1000 bp). Thus, experiments were conducted to test gDNA from PBMCs that is sheared to provide DNA of a smaller size. DNA was sheared as described above (e.g., by needle and Covaris S2 sonication).

Commercially available gDNA contains diploid genomes, wild-type KRAS, and unmethylated markers (e.g., BMP3 and NDRG4). Since methylated BMP3 and NDRG4 markers and KRAS mutations are not present in this DNA source, providing a control having the desired methylation status and mutations would involve the addition of mutated DNA and methylated DNA to provide a suitable control mimicking DNA obtained from a stool sample. The mutated and methylated DNA would be provided from another source, e.g., as described throughout this disclosure.

In sum, purified gDNA from PBMCs does not provide a feasible source of DNA for manufacturing DNA controls. In particular, PBMC gDNA does not provide methylated BMP3 and NDRG4 markers. As such, in vitro methylation would be required. However, as discussed above, in vitro methylation is an inefficient and uncontrolled process that is not suitable for manufacturing the DNA controls according to the technology provided herein. Furthermore, PBMC gDNA does not provide KRAS mutations and, thus, an alternate source of mutation marker DNA would be required. To meet the safety and performance requirements for the colorectal cancer screening assays, reagents must be reproducible from lot to lot. Therefore, the use of gDNA from PBMCs was not viable.

Consequently, stool DNA was investigated as a source of gDNA to use for a control DNA reagent. It was contemplated that stool DNA could be used as run controls for the colorectal cancer screening assay by either purifying the DNA from stool or by using actual stool samples, either individual or pooled. One advantage of this approach is that stool DNA would not need to be processed to obtain shorter fragments as the DNA in stool samples is already fragmented. During the development of the colorectal cancer screening assay, positive stool samples were successfully used for development and during analytical verification studies. However, there is no commercial source for stool samples and a constant supply of positive material would be difficult to sustain. Thus, it was concluded that stool DNA is not feasible for manufacturing DNA controls.

Example 2—Plasmid DNA

As an alternative to genomic DNA, experiments were conducted to assess the suitability of plasmid DNA for DNA controls. In particular, as a large supply of high quality plasmid material can be easily obtained and copy numbers are quantifiable, plasmids were evaluated for use as DNA control targets. Plasmids were designed containing marker sequences; the marker sequences were designed to be excised from the plasmid vector by EcoRI digestion. While ACTB and KRAS markers are feasible in a plasmid format, methylated targets are not. Therefore, either an independent source of methylated targets was needed or plasmids needed to be methylated (e.g., by an in vitro method). Accordingly, experiments were performed to evaluate a plasmid methylation process. As a result, it was determined that plasmids need to be column purified prior to in vitro methylation. This process results in an estimated 10% loss of material. Then, in vitro methylation experiments and assays indicated that plasmids methylated in vitro generated signals in QuARTS methylation assays. Next, experiments were performed to improve the methylation reaction by varying the template concentration, enzyme concentration, incubation temperature, and incubation time. At optimal conditions, 85% recovery (final measured signal compared to theoretical maximum) was observed in the QUARTS methylation assay. As a result of these experiments, it was concluded that plasmids are not feasible for manufacturing DNA controls and that in vitro methylation is not a feasible manufacturing process.

Example 3—Synthetic DNA

The experiments demonstrating unsatisfactory production of fully methylated plasmids indicated that producing the DNA controls required identifying a consistently methylated DNA source. It was contemplated that synthesized DNA would provide such a source. For example, synthetic methods of DNA production can produce methylated oligonucleotide targets by incorporating methylcytosines during the synthesis process. Moreover, oligonucleotides comprising KRAS mutation targets are easily manufactured.

Figure 2A:
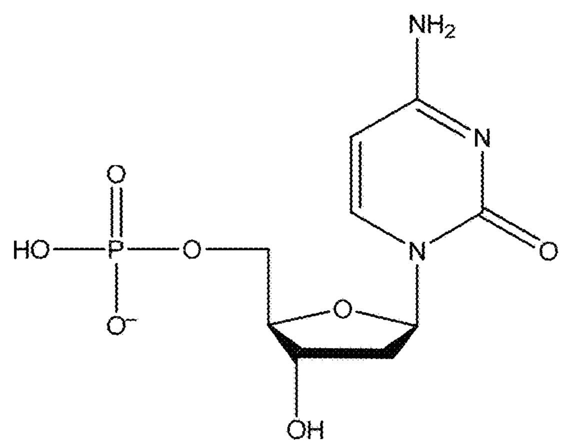
FIGS. 2A-C show the chemical structures of methylated and unmethylated cytosines.
Figure 2B:
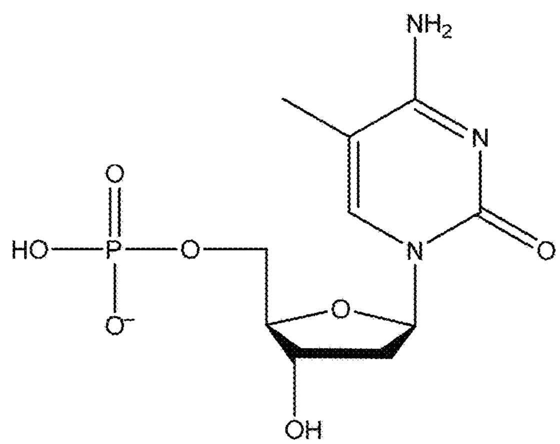
Figure 2C:
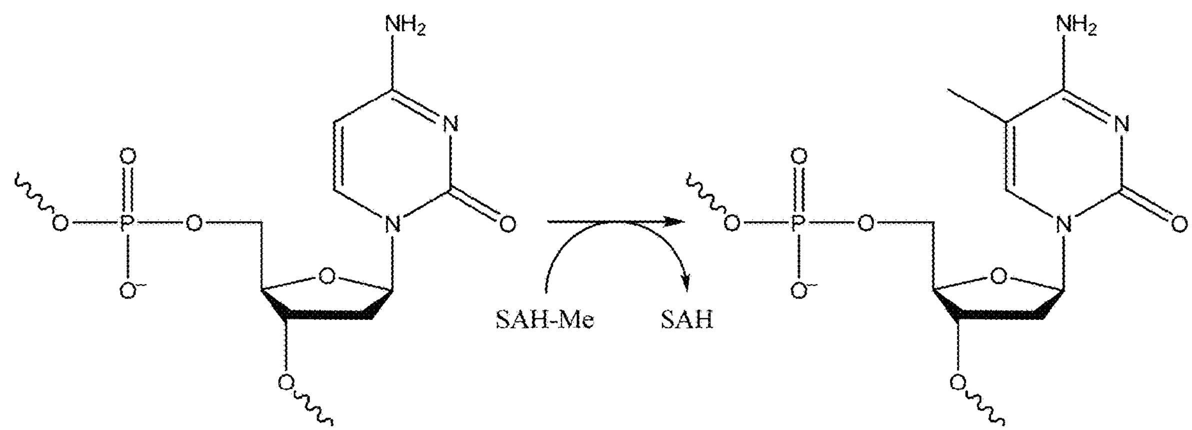

The chemical structures of deoxycytosine and 5-methyldeoxycytosine are shown in FIG. 2A and FIG. 2B, respectively. In vivo methylation is diagrammed in FIG. 2C to show that an in vivo methylated cytosine is equivalent to the 5-methyl-dC used for synthesis of synthetic DNA targets.

To assess processes for producing a control comprising synthesized methylated targets, four oligonucleotides were designed (Table 6). The oligonucleotides were designed to represent both wild-type NDRG4 sequence and methylated NDRG4 sequence. In addition, oligonucleotides were designed to represent the wild-type and methylated sequences after bisulfate conversion, e.g., in which unmethylated cytosines are converted to uracil.

TABLE 8

Description of Initial NDRG4 Oligos

| Oligonucleotide Designation | Oligonucleotide Name | CG | C | Description |
|---|---|---|---|---|
| 1 | NDRG4-WT | CG | C | Unmethylated wild type NDRG4 sequence |
| 2 | NDRG4-WT-BST | UG | U | Wild type NDRG4 sequence after bisulfite conversion |
| 3 | NDRG4-Me | 5-methyl-dCG | C | Methylated NDRG4 sequence |
| 4 | NDRG4-Me-BST | CG | U | Methylated NDRG4 sequence after bisulfite conversion |

Figure 3:
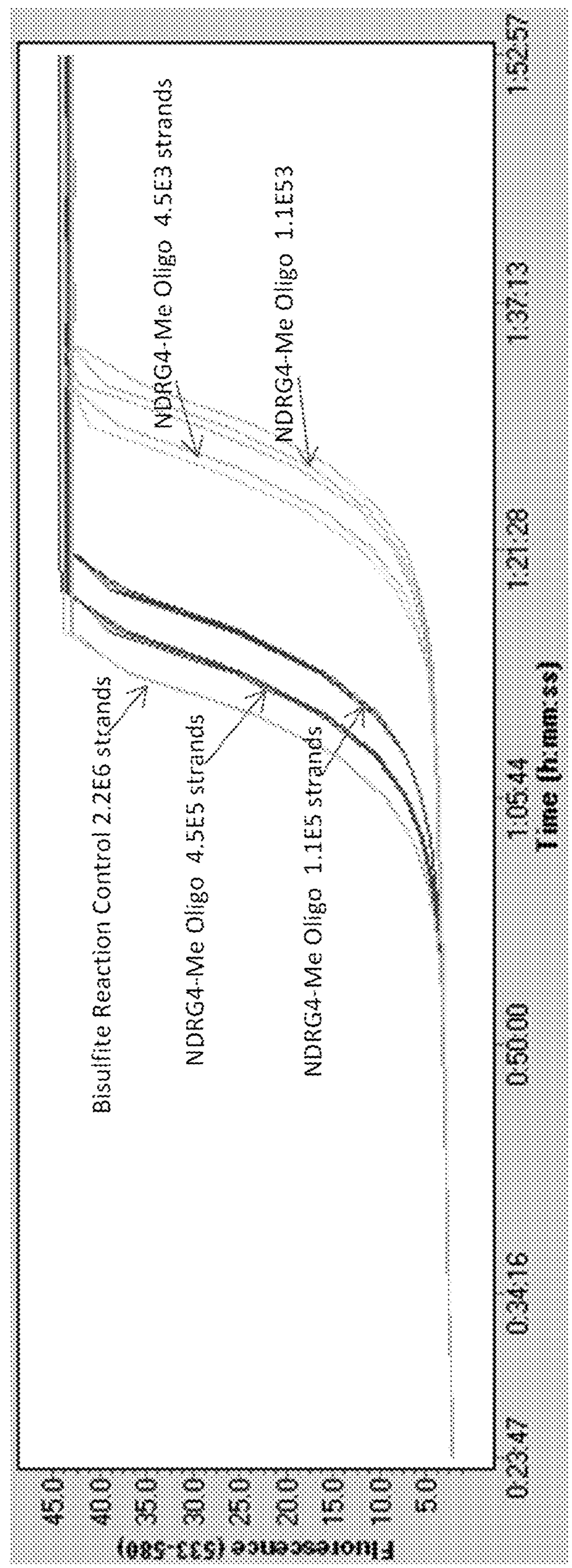
FIG. 3 is a plot showing QuARTS assay amplification curves for an embodiment of the methylated NDRG-4 (NDRG4-Me) oligonucleotide designed and tested during the development of the technology described herein. Test oligonucleotides were ordered from a commercial supplier (Integrated DNA Technologies, Coralville, Iowa). Oligonucleotides were tested by processing the NDRG4-Me oligonucleotide through a bisulfate conversion reaction column overnight (Zymo column, Zymo Research, Irvine Calif.) and detecting the converted oligonucleotides by QuARTS methylation assay. Signal was detected and was observed to increase with increasing target concentration, indicating the oligonucleotides could be converted and detected using standard methods.

The four test oligonucleotides were purchased from Integrated DNA Technologies (IDT, Coralville, Iowa). In Table 8, the “CG” and “C” columns indicate the base incorporated at CG positions and C positions for each oligonucleotide relative to the wild-type sequence. That is, for every CG in the wild-type NDRG4 sequence, oligonucleotides 2, 3, and 4 had a UG, 5-Me-CG, and CG at the same positions of their sequences respectively; for every C in the wild-type NDRG4 sequence that was not in a CG dinucleotide, oligonucleotides 2, 3, and 4 had a U, C, and U at the same positions of their sequences, respectively. The functionality of the oligonucleotides was assessed by performing a bisulfite reaction on Oligonucleotide 3 (e.g., overnight reaction with a Zymo bisulfite reaction column) and detecting the converted oligonucleotides in the QUARTS methylation assay. A signal was detected and it increased with increasing target concentration, thus indicating that the oligonucleotide was methylated (e.g., unconverted) and could be subsequently detected by the methylation assay (Table 9 and FIG. 3).

TABLE 9

Test of 5-methyl-dC Modified Oligo

| Oligonucleotide Designation (from Table 8) | Sample Description | Strands into QuARTS assay | Mean Strands Recovered, in QuARTS assay |
|---|---|---|---|
| NA | Bisulfite Reaction Control | 9,999 | 7,294 |
| 3 | NDRG4-Me | 2,001 | 4,227 |

TABLE 9-continued

Test of 5-methyl-dC Modified Oligo

| Oligonucleotide Designation (from Table 8) | Sample Description | Strands into QuARTS assay | Mean Strands Recovered, in QuARTS assay |
|---|---|---|---|
| 3 | NDRG4-Me | 1,001 | 2,146 |
| 3 | NDRG4-Me | 20 | 155 |
| 3 | NDRG4-Me | 10 | 76 |

Furthermore, experiments were conducted to screen for potential contamination of oligonucleotides during manufacturing (e.g., cross-contamination of one oligonucleotide type with another oligonucleotide type). In particular, NDRG4 oligonucleotides were tested directly in the QUARTS methylation assay without bisulfite conversion. The concentrations tested comprised $10^6$ strands per reaction with 10-fold dilutions down to 1 strand per reaction. A signal was detected for the NDRG4-Me-BST oligonucleotide only and not for the other oligonucleotides (Table 10), indicating that contamination with NDRG4-Me-BST oligonucleotide during manufacturing was not detectable.

TABLE 10

Testing NDRG4 Oligonucleotides Directly in QuARTS Assay

| Oligonucleotide Designation (from Table 8) | Oligonucleotide Name | Oligonucleotide Description | Expected Results | Actual Results |
|---|---|---|---|---|
| 1 | NDRG4-WT | Wild type NDRG4 sequence | Negative for all concentrations | Negative for all concentrations |
| 2 | NDRG4-WT-BST | Wild type NDRG4 sequence after bisulfite conversion | Negative for all concentrations | Negative for all concentrations |
| 3 | NDRG4-Me | Methylated NDRG4 sequence | Negative for all concentrations | Negative for all concentrations |
| 4 | NDRG4-Me-BST | Methylated NDRG4 sequence after bisulfite conversion | Strand results similar to calculated inputs | Average of 40% of expected results for all concentrations |

NDRG4 oligonucleotides were screened by processing them through the bisulfite conversion reaction (e.g., overnight reaction with a Zymo bisulfite reaction column) before assessing methylation status in the QuARTS methylation assay. The concentrations tested were $10^4$ strands per sample with 10-fold dilutions down to 100 strands per sample. No cross reactivity was detected (Table 11).

TABLE 11

Testing NDRG4 Oligonucleotides Through Bisulfite Conversion

| Oligonucleotide Designation (from Table 8) | Oligonucleotide Name | Oligonucleotide Description | Expected Results | Actual Results |
|---|---|---|---|---|
| 1 | NDRG4-WT | Wild type NDRG4 sequence | Negative for all concentrations | Negative for all concentrations |
| 3 | NDRG4-Me | Methylated NDRG4 sequence | Positive | Average of 60% expected recovery for all concentrations |

Following on the results of the experiments above testing NDRG4, BMP3 oligonucleotides were designed, purchased, and tested using the same strategies as for the NDRG4 oligonucleotides described above. The oligonucleotide BMP3-Me-BST (e.g., representing methylated BMP3 sequence after bisulfite conversion) showed an average of 50% expected recovery when tested directly in the QUARTS methylation assay. However, a signal was detected for BMP3-WT (e.g., representing unmethylated wild type BMP3 sequence) and BMP3-WT-BST (e.g., representing wild type BMP3 sequence after bisulfite conversion) when tested directly in the QUARTS methylation assay, indicating that the targets were contaminated. Follow-up testing of the oligonucleotide stocks indicated that oligonucleotide contamination occurred during manufacturing at the supplier.

The following test oligonucleotides for ACTB were designed, manufactured by the supplier, and tested as described above for NDRG4 and BMP3 oligonucleotides (Table 12).

TABLE 12

Description of ACTB Oligos

| Oligonucleotide Designation | Oligonucleotide Name | Description |
|---|---|---|
| 1 | ACTB-WT | ACTB wild type sequence |
| 2 | ACTB-WT-BST | ACTB-WT after bisulfite conversion |

The ACTB-WT-BST oligonucleotide was detected when tested directly in the QuARTS methylation assay (Table 13). No strands were detected from the ACTB-WT oligonucleotide samples when tested directly in the methylation assay (Table 13); this is the expected result as the ACTB sequence must be converted to be detected in the Methylation Assay. Both ACTB oligonucleotides were detected when processed through the Zymo overnight bisulfite reaction (Table 13).

TABLE 13

Testing ACTB Oligos

| | | Direct Testing in QuARTS Methylation Assay | | Processing Through Bisulfite Conversion followed by QuARTS Methylation Assay | |
|---|---|---|---|---|---|
| Oligonucleotide Designation | Oligonucleotide Name | Expected Results | Actual Results | Expected Results | Actual Results |
| 1 | ACTB-WT | Negative for all concentrations | Negative for all concentrations | positive | Average of 30% expected recovery for all concentrations |
| 2 | ACTB-WT-BST | Strand results similar to calculated inputs | Average of 50% expected recovery for all concentrations | unknown | Average of 30% expected recovery for all concentrations |

Further experiments were conducted during the development of embodiments of the technologies described herein to test a magnetic bead desulfonation process on the NDRG4, BMP3, and ACTB oligonucleotides. Recoveries were up to 60%, indicating that synthetic targets provide a suitable source of DNA to produce the control DNA sample for the colorectal cancer screening assay.

Experiments were also conducted to assess target multiplexing by combining ACTB-WT, NDRG4-Me, and BMP3-Me oligonucleotides in varying ratios. The results show that multiplexing was successful (Table 14)

TABLE 14

Target Recoveries from Multiplexed Sample

| | Targeted Copies per Reaction | | Average Copies Recovered (n = 3) | | | Average % Recovery (n = 3) | | |
|---|---|---|---|---|---|---|---|---|
| Sample | ACTB | NDRG4/ BMP3 | ACTB | NDRG4 | BMP3 | % ACTB | % NDRG4 | % BMP3 |
| 1 | 10000 | 2000 | 4970 | 988 | 855 | 50% | 49% | 43% |
| 2 | 10000 | 2000 | 5580 | 1260 | 961 | 56% | 63% | 48% |
| 3 | 10000 | 200 | 5777 | 287 | 209 | 58% | 144% | 104% |
| 4 | 10000 | 200 | 4729 | 224 | 171 | 47% | 112% | 86% |
| 5 | 2000 | 200 | 1013 | 100 | 101 | 51% | 50% | 51% |
| 6 | 2000 | 200 | 1203 | 155 | 135 | 60% | 78% | 67% |

Figure 4:
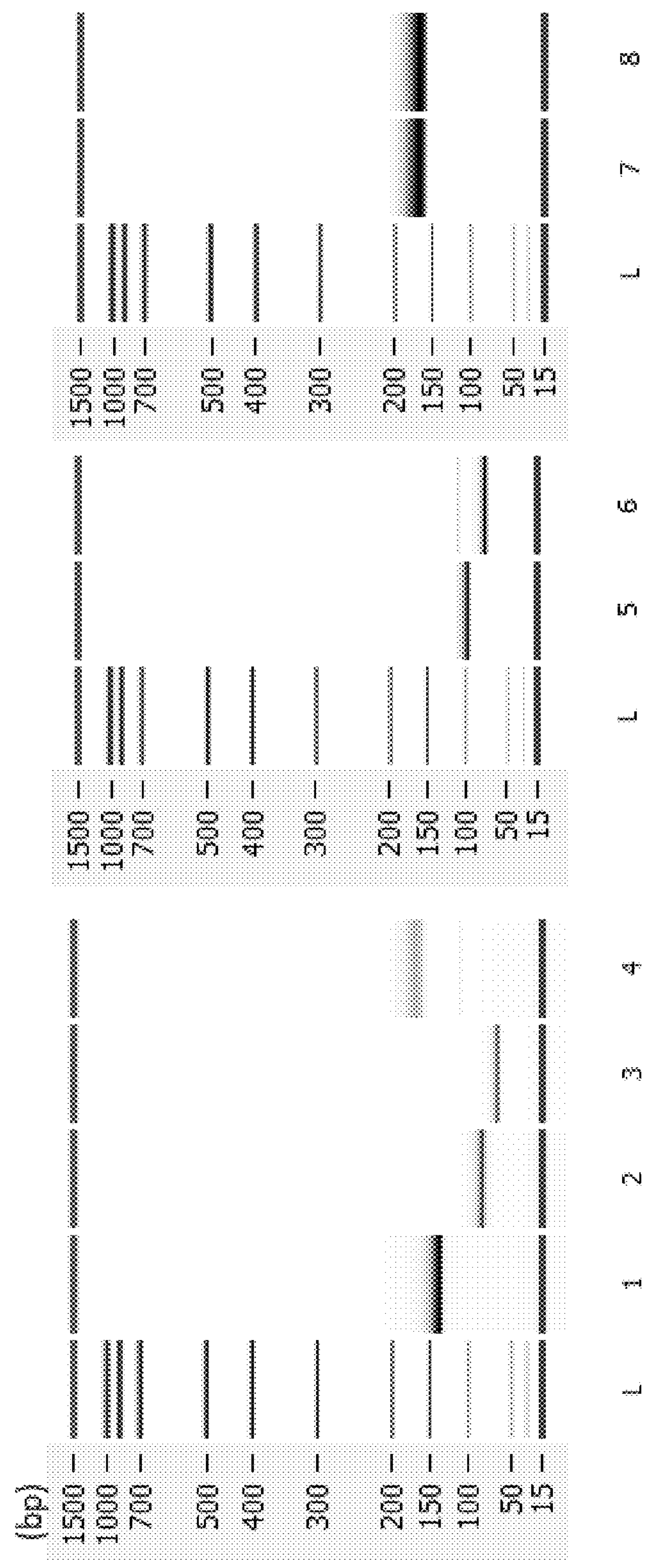
FIG. 4 is a plot from Bioanalyzer analysis showing the sizes of double stranded oligonucleotides produced as described herein. The lanes in each panel are as follows: L is a DNA size ladder standard; lanes labeled 1 through 8 show results for the double stranded oligonucleotides, respectively: PCTRL-ACTB-WT-ds, PCTRL-NDRG4-WT-ds, PCTRL-BMP3-WT-ds, PCTRL-KRAS-WT-ds, PCTRL-NDRG4-ME-ds, PCTRL-BMP3-ME-ds, PCTRL-KRAS-38A-ds, and PCTRL-KRAS-35C-ds.

During sample processing, sense strands of ACTB, NDRG4, and BMP3 targets are captured and both sense and anti-sense strands of the KRAS target are captured. Accordingly, the DNA controls were designed to comprise double-stranded DNA for all targets to mimic the DNA present in stool samples as well as to include both strands for the KRAS targets. To create double-stranded targets from single-stranded oligonucleotides, complimentary sequences were synthesized by the supplier and annealed. An annealing protocol was developed based on a process from Cwirla et al (1990) "Peptides on phage: A vast library of peptides for identifying ligands" Proc. Natl. Acad. Sci. USA 87: 6378-6382, incorporated herein by reference in its entirety. Annealed oligonucleotides were analyzed on the Bioanalyzer using the Agilent DNA 1000 Kit (5067-1504). Results indicated that the annealing process was successful (FIG. 4).

Experiments were also conducted to compare single-stranded targets to double-stranded targets by testing KRAS 38A oligonucleotides in a single-plex QUARTS mutation assay and NDRG4 and BMP3 oligonucleotides in the full capture, conversion, and QUARTS processes. Results show that annealed oligonucleotides were recovered in both cases (Table 15 and Table 16).

TABLE 15

Recovery of Single-Stranded and Double-Stranded KRAS Oligonucleotide Targets in QuARTS Assay

| KRAS Target | Input strands per reaction | Average Strands Recovered (N = 3) | Average % Recovery |
|---|---|---|---|
| Sense | 1,000,000 | 621,847 | 62% |
| Sense | 100,000 | 75,998 | 76% |
| Sense | 10,000 | 9,136 | 91% |
| Sense | 1,000 | 1,049 | 105% |
| Sense | 100 | 125 | 125% |
| Sense | 10 | 13 | 130% |
| Sense | 1 | 3 | 300% |
| Anti-sense | 1,000,000 | 580,283 | 58% |
| Anti-sense | 100,000 | 72,055 | 72% |
| Anti-sense | 10,000 | 9,027 | 90% |
| Anti-sense | 1,000 | 931 | 93% |
| Anti-sense | 100 | 103 | 103% |
| Anti-sense | 10 | 14 | 140% |
| Anti-sense | 1 | 4 | 400% |
| Double-stranded | 2,000,000 | 1,183,124 | 59% |
| Double-stranded | 200,000 | 151,348 | 76% |
| Double-stranded | 20,000 | 18,627 | 93% |
| Double-stranded | 2,000 | 2,166 | 108% |
| Double-stranded | 200 | 244 | 122% |
| Double-stranded | 20 | 24 | 120% |
| Double-stranded | 2 | 1 | 50% |

TABLE 16

Recovery of Double-Stranded NDRG4 and BMP3 Oligonucleotide Targets in Capture, Conversion, and QuARTS assay

| Target | Mean % recovery |
|---|---|
| Double-stranded NDRG4-Me | 28% |
| Double-stranded BMP3-Me | 12% |

Initial sequence designs comprised only the capture footprint (the sequence used for capture by the capture oligonucleotide) and the QuARTS footprint (e.g., the methylation footprint, the sequence used to test for methylation assay) for each target. The shortest target design, BMP3, comprising 55 nucleotides, is shown in FIG. 5. Original oligonucleotide designs minimized sequence length due to the complexities of synthesizing longer oligonucleotides. BMP3 recovery through capture, bisulfite conversion, and QUARTS assay was inconsistent, whereas the other targets demonstrated more reproducible performance. Analysis of the data collected from testing the various oligonucleotides indicated that the inconsistent performance was due to the BMP3 target design. Accordingly, experiments were conducted to test assay performance as a function of the positions of the footprints relative to the ends of the oligonucleotides and as affected by oligonucleotide length.

The two shorter oligonucleotide targets, NDRG4 and BMP3, were redesigned to include flanking gene sequence so that lengths of the BMP3, NDRG4, and ACTB oligonucleotides were all the same (e.g., 126 nt). The 126-nt oligonucleotides showed improved performance. Based on these data, oligonucleotides were redesigned (see FIG. 6).

Using recovery data obtained from earlier experiments, formulations for high, low, and negative process controls were prepared to evaluate multiplexing and attaining the signals required for useful DNA controls. The data collected (Table 17 and Table 18) indicate that multiplexing and detecting a signal of the desired strand output for a set of high, low, and negative controls was successful using the synthetic DNA targets. The data from these experiments show that when mixed as the high, low, or negative multiplexes, results similar to what are expected are generated. This includes both net number of strands and percentage mutation or percentage methylation.

TABLE 17

Multiplexing Results

| Process Control | ACTB (KRAS) strands Mean | 38A strands Mean | 35C strands Mean | ACTB (ANB) strands Mean | NDRG4 strands Mean | BMP3 strands Mean |
|---|---|---|---|---|---|---|
| High | 14395 | 1313 | 1437 | 5999 | 855 | 907 |
| Low | 14947 | 482 | 521 | 5859 | 533 | 560 |
| Negative | 697 | 4 | 6 | 306 | 0 | 0 |

TABLE 18

Multiplexing Results

| Process Control | NDRG4 % Methylation Mean | BMP3 % Methylation Mean | 38A % Mutation Mean | 35C % Mutation Mean |
|---|---|---|---|---|
| High | 16.29% | 17.85% | 9.07% | 9.65% |
| Low | 11.22% | 11.97% | 3.39% | 3.33% |
| Negative | 0.06% | 0.00% | 0.42% | 0.64% |

In sum, the data collected demonstrated that high, low, and negative control samples comprising synthetic oligonucleotide targets provide satisfactory materials for manufacturing DNA controls. As such, embodiments of the technology provided herein relate to DNA controls comprising synthetic DNA targets. Advantages of this technology relative to conventional solutions include control of the compositions of the synthetic oligonucleotides, which are manufactured to comprise a specific sequence. Syntheses are designed to produce oligonucleotides representing methylation and mutation markers. Synthesized oligonucleotides are purified and quantitated allowing for consistent formulation of DNA controls. Oligonucleotide lengths are similar to stool DNA fragment sizes and behave similarly to stool DNA in the purification and assay process.

Example 4—Matrix

During the development of embodiments of the technology provided herein, experiments were conducted to test buffer formulations for the DNA controls. In these experiments, the following factors were tested: functional performance, preservative properties, and similarity to stool samples. Experiments tested two types of buffer compositions:

1) 10 mM Tris, 1 mM EDTA was tested because it is a common buffer for nucleic acids. Buffers at pH 7.5, pH 8.0, and pH 9.0 were tested.

2) DNA Stabilization Buffer (500 mM Tris-HCl, 150 mM EDTA, 10 mM NaCl, pH 9) was tested because stool samples are stored in DNA Stabilization Buffer with a final composition of 20% stool and 80% DNA Stabilization Buffer. Solutions comprising 80% DNA Stabilization Buffer and 100% DNA Stabilization Buffer were tested.

Evaluation of functional performance showed that DNA controls formulated in 10 mM Tris, 1 mM EDTA were recovered at lower concentrations compared to DNA controls formulated in DNA Stabilization Buffer. During additional experiments, data indicated that the lower signals were due to ineffective magnetization of the capture beads and subsequent loss of beads during aspiration. DNA Stabilization Buffer improved magnetization of the capture beads compared to the Tris/EDTA formulation.

Additionally, treatment of the DNA Controls with an inhibitor removal tablet and spin filter prior to capture increased signal recovery. Based on this observation, it was decided that DNA controls would be processed in parallel with the test samples beginning at the step where an inhibitor tablet is added to 14 ml of test sample supernatant.

Stool samples are typically homogenized and processed in a final ratio of 20% stool to 80% DNA Stabilization Buffer; therefore, the DNA Control formulation that is most similar to stool samples is 80% DNA Stabilization Buffer. Based on aspect of the sample processing and the data collected comparing the performances of the buffer types, 80% DNA Stabilization Buffer was chosen as the DNA control buffer formulation and that DNA controls would be processed alongside stool samples starting with inhibitor removal tablet treatment.

In addition, experiments were conducted during the development of embodiments of the technology provided herein to assess the effects of non-target nucleic acids (e.g., "nucleic acid background") in the DNA controls. In particular, dilute nucleic acid solutions are often supplemented with a nucleic acid background to prevent binding of critical nucleic acid material to plastic. Accordingly, experiments were conducted to evaluate the yeast tRNA and fish sperm DNA as nucleic acid components for use in the formulation of the DNA controls. Based on the data collected, fish sperm DNA was chosen for the final formulation based on its performance in colorectal cancer assay, price, and previous use in the manufacture of other DNA controls. Fish DNA concentrations were evaluated using the QuARTS mutation assay. Results showed samples with 20 μg/mL fish DNA lost approximately 30% of signal compared to samples prepared with 50 μg/mL fish DNA. Samples with 100 μg/mL fish DNA showed no statistical difference from samples with 50 μg/mL fish DNA. Based on these results, 50 μg/mL fish DNA was used for the final formulation of the DNA control.

Example 5—Storage and Stability

During the development of embodiments of the technology provided herein, experiments were conducted to test the stability of the DNA controls. In particular, several strategies were evaluated for protecting the synthetic DNA from degradation during storage. In some embodiments, DNA controls are stored at a temperature above freezing, e.g., at +4° C., while in some embodiments, −20° C. storage is appropriate. In addition, 0.05% sodium azide does not affect functional performance and some embodiments include sodium azide (e.g., at 0.05%), for example, embodiments that do not comprise a DNA Stabilization Buffer. Some embodiments comprise DNA Stabilization Buffer, e.g., containing 150 mM EDTA and 10 mM NaCl, as may be used for stabilization of DNA in stool samples tested in screening for colorectal cancer.

Figure 7A:
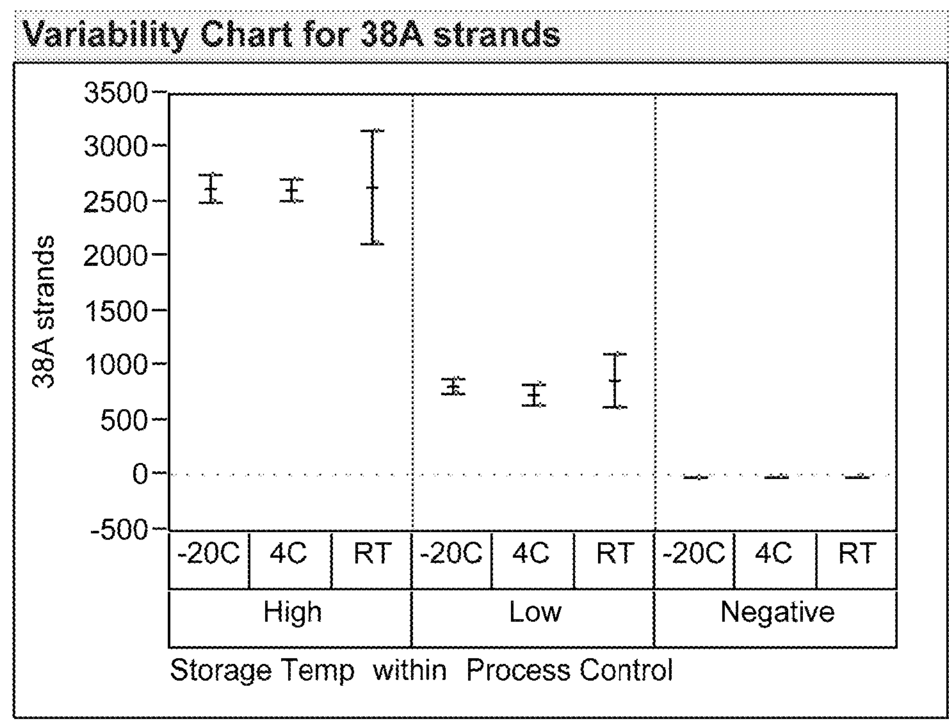
FIGS. 7A and 7B show a series of plots showing the integrity of embodiments of the control DNA provided by the technology described herein after storage, e.g., at −20° C., 4° C., and at room temperature.
Figure 7B:
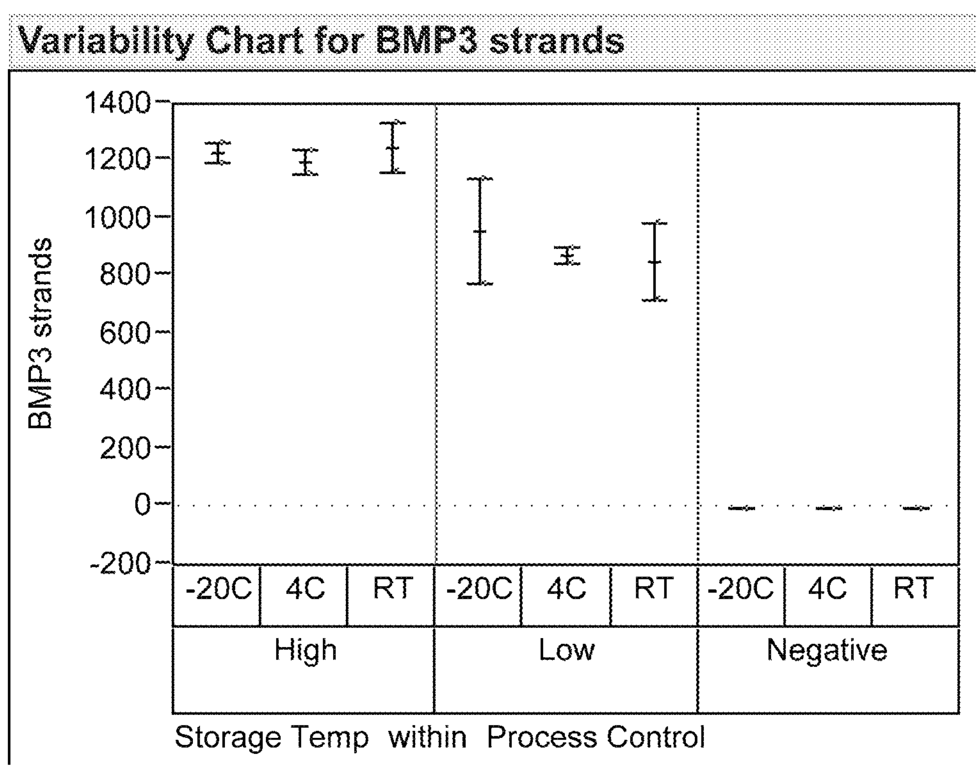

Experiments were conducted to compare storage at different temperatures, in particular, by comparing performance of the High, Low, and Negative DNA controls at different temperatures after six months of storage at −20° C., +4° C., or at room temperature (RT). The data collected for the strands detected in assays performed on the stored DNA controls indicate that the DNA control material is robust with respect to storage temperature (FIG. 7).

Example 6—Guard Band Evaluation

During the development of embodiments of the technology provided herein, experiments were conducted to assess if the DNA controls provide adequate signal when processed with +/−10% of the required volume for a typical assay. In particular, two lots of DNA controls were processed at +/−15% of the required volume through the colorectal cancer screening process and assay. Data collected indicated that all run validity specifications were met for all lots of DNA controls when processed at 85%, 100%, and 115% of required volume (FIG. 8).

Example 7—DNA Control Sample Formulation

During the development of embodiments of the technology described herein, DNA control formulations were prepared according to the data collected and design guidelines relating to production of a satisfactory control. In some embodiments, the DNA controls are formulated with double-stranded oligonucleotide targets as indicated in Table 19. Wild-type oligonucleotide targets are included to represent wild-type sequence that is present in a stool sample, although these targets do not give a positive signal in the colorectal cancer screening assay. In some embodiments, the sequences of the oligonucleotides are as indicated in FIG. 6.

TABLE 19

Targets Present in DNA Control

| Target | DNA Control 1, High | DNA Control 2, Low | DNA Control 3, Negative |
|---|---|---|---|
| ACTB | x | x | x |
| KRAS 38A | x | x | |
| KRAS 35C | x | x | |
| KRAS WT | x | x | x |
| NDRG4 Me | x | x | |
| NDRG4 WT | x | x | x |
| BMP3 Me | x | x | |
| BMP3 WT | x | x | x |

In some embodiments, DNA Control 1 (High) and DNA Control 2 (Low) comprise target ACTB strands level at approximately 50,000 strands as determined in the ACTB mutation assay. This value represents the average ACTB level observed in colorectal cancer positive samples. In some embodiments, DNA Control 3 (Negative) comprises a target ACTB strands level at approximately 15,000 strands as determined in the ACTB mutation assay. This value represents the average ACTB level observed in colorectal cancer negative samples. DNA Control 2 (Low) levels for methylation and mutation markers are set at one percent (1%) above the assay cutoffs as established by data collected in experiments to establish assay cutoffs (Table 20). In some embodiments, DNA Control 1 (High) target levels for methylation and mutation markers are set at two times (2×) the target levels set for DNA Control 2 (Low) (Table 20)

TABLE 20

Design Target Levels for % Methylation and % Mutation

| Marker | Cutoff Values Established in DD-0224 % Methylation | Cutoff Values Established in DD-0224 % Mutation | Target for DNA Control 2, Low % Methylation | Target for DNA Control 2, Low % Mutation | Target for DNA Control 3, High % Methylation | Target for DNA Control 3, High % Mutation |
|---|---|---|---|---|---|---|
| NDRG4 | 4.5% | | 5.5% | | 11% | |
| BMP3 | 0.6% | | 1.6% | | 3.2% | |
| KRAS 38A | | 2.0% | | 3.0% | N/A | 6% |
| KRAS 35C | | 3.7% | | 4.7% | N/A | 9.4% |

Following the guidelines established above, targeted strand levels for some embodiments of the DNA controls were set (Table 21).

TABLE 21

Design Targets for Strand Output per Marker

| DNA Control | ACT Mutation Assay | BTACT Methylation Assay | NDRG4-Me | BMP3-Me | KRAS 38A | KRAS 35C |
|---|---|---|---|---|---|---|
| 1, High | 50,000 | 25,000 | 2,750 | 800 | 3,000 | 4,700 |
| 2, Low | 50,000 | 25,000 | 1,375 | 400 | 1,500 | 2,350 |
| 3, Negative | 15,000 | 7,500 | 0 | 0 | 0 | 0 |

Further experiments were performed to evaluate the copy number input required to obtain the targeted strand outputs determined above. In particular, experiments were conducted to titrate input oligonucleotide concentrations and then evaluate the results when processed through the colorectal cancer screening workflow. The data were used to determine the number of input copies of each DNA to produce the design targets for strand output (Table 22).

TABLE 22

Input Required to Hit Targeted Output

| DNA Control | Copies/mL dsDNA ACTB | KRAS 38A | KRAS 35C | NDRG4 Me | BMP3 Me | KRAS WT | NDRG4 WT | BMP3 WT |
|---|---|---|---|---|---|---|---|---|
| 1, High | 200,000 | 2,800 | 5,800 | 14,000 | 5,500 | 50,000 | 50,000 | 50,000 |
| 2, Low | 200,000 | 1,000 | 2,500 | 6,000 | 2,200 | 50,000 | 50,000 | 50,000 |
| 3, Negative | 66,000 | NA | NA | NA | NA | 16,500 | 16,500 | 16,500 |

Based on data collected during the development of embodiments of the technology provided herein, DNA controls were produced comprising the input copies of each target in a buffer to provide a control reagent. In some embodiments, the control reagent comprises 80% DNA Stabilization Buffer (500 mM Tris, 150 mM EDTA, and 10 mM NaCl, pH 9) plus 50 ng/mL fish DNA. Embodiments of the High DNA control, Low DNA control, and Negative DNA control are provided below (Table 23, Table 24, and Table 25).

TABLE 23

Formulation of DNA Control 1, High

| Concentration | | Description |
|---|---|---|
| 2.0E+05 | copies/mL | PCTRL-ACTB-WT-ds |
| 5.0E+04 | copies/mL | PCTRL-KRAS-WT-ds |
| 5.0E+04 | copies/mL | PCTRL-126-NDRG4-WT-ds |
| 5.0E+04 | copies/mL | PCTRL-126-BMP3-WT-ds |
| 2.8E+03 | copies/mL | PCTRL-KRAS-38A-ds |
| 5.8E+03 | copies/mL | PCTRL-KRAS-35C-ds |
| 1.4E+04 | copies/mL | PCTRL-126-NDRG4-ME-ds |
| 5.5E+03 | copies/mL | PCTRL-126-BMP3-ME-ds |
| 80 | % | DNA Stabilization Buffer |
| 50 | ng/mL | Fish Sperm DNA |

TABLE 24

Formulation of DNA Control 2, Low

| Concentration | | Description |
|---|---|---|
| 2.0E+05 | copies/mL | PCTRL-ACTB-WT-ds |
| 5.0E+04 | copies/mL | PCTRL-KRAS-WT-ds |
| 5.0E+04 | copies/mL | PCTRL-126-NDRG4-WT-ds |
| 5.0E+04 | copies/mL | PCTRL-126-BMP3-WT-ds |
| 1.0E+03 | copies/mL | PCTRL-KRAS-38A-ds |
| 2.5E+03 | copies/mL | PCTRL-KRAS-35C-ds |
| 6.0E+03 | copies/mL | PCTRL-126-NDRG4-ME-ds |
| 2.2E+03 | copies/mL | PCTRL-126-BMP3-ME-ds |
| 80 | % | DNA Stabilization Buffer |
| 50 | ng/mL | Fish Sperm DNA |

TABLE 25

Formulation of DNA Control 3, Negative

| Concentration | | Description |
|---|---|---|
| 6.6E+04 | copies/mL | PCTRL-ACTB-WT-ds |
| 1.7E+04 | copies/mL | PCTRL-KRAS-WT-ds |
| 1.7E+04 | copies/mL | PCTRL-126-NDRG4-WT-ds |
| 1.7E+04 | copies/mL | PCTRL-126-BMP3-WT-ds |
| 80 | % | DNA Stabilization Buffer |
| 50 | ng/mL | Fish Sperm DNA |

Figure 9:
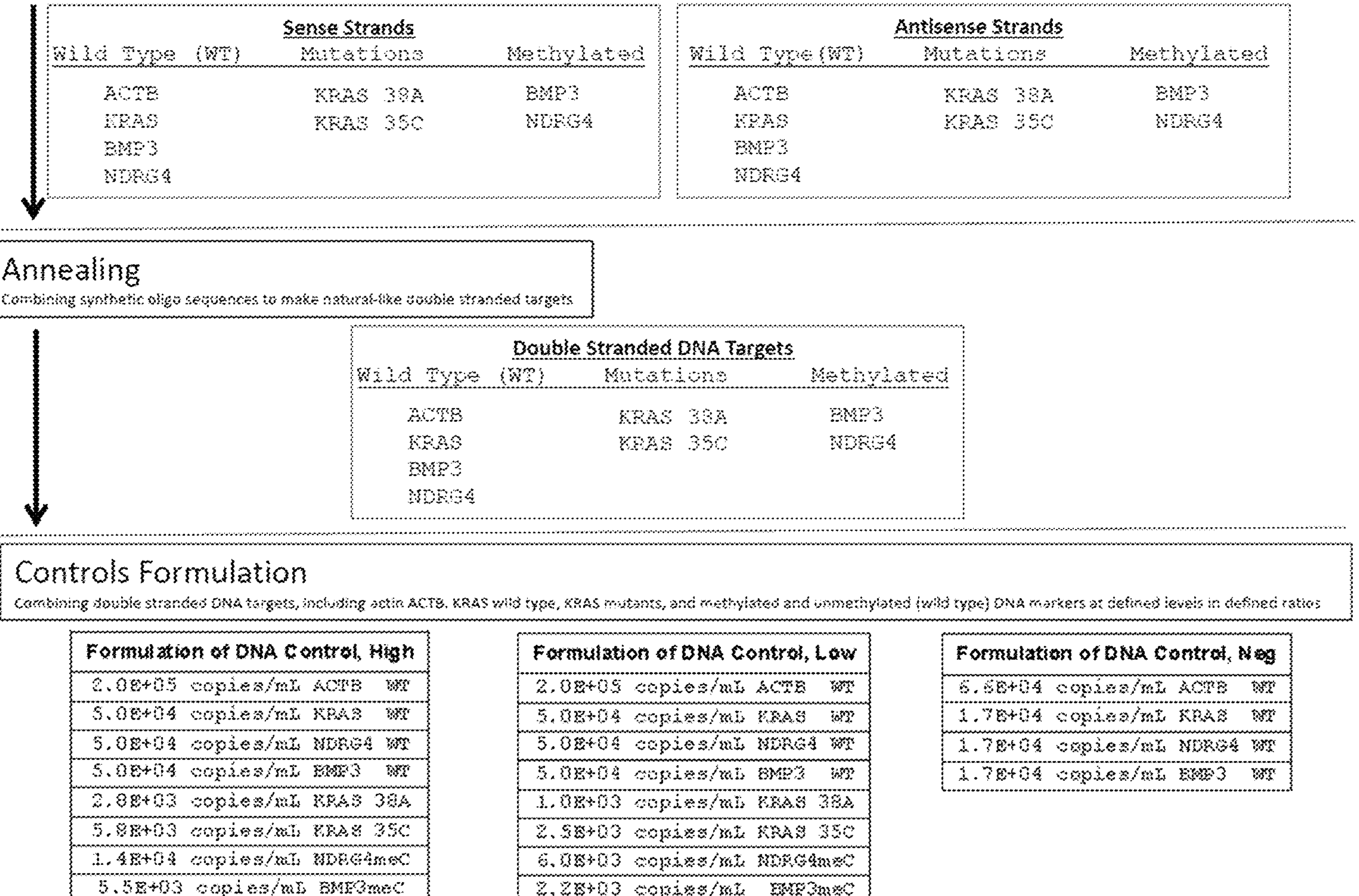
FIG. 9 is a diagram showing a method embodiment of the technology described herein, and formulations of certain embodiments of the technology.

In some embodiments, the controls are produced according to a process as follows (see, e.g., FIG. 9). DNA is synthesized according to the sequence and methyl-C positions desired. DNA synthesis is provided by an automated DNA synthesizer and stock solutions of the four standard A, T, C, and G bases in addition to 5-methyl-C. In some embodiments, single-stranded oligonucleotides are made comprising sequences from wild-type ACTB, KRAS, BMP3, and NDRG4; the KRAS 38A and KRAS 35C mutations; and methylated BMP3 and methylated NDRG4. In some embodiments, both sense and antisense (complementary) single-stranded oligonucleotides are made comprising sequences or complementary sequences from wild-type ACTB, KRAS, BMP3, and NDRG4; the KRAS 38A and KRAS 35C mutations; and methylated BMP3 and methylated NDRG4. Then, in some embodiments the single-stranded oligonucleotides are annealed (e.g., by heating and cooling, e.g., at a controlled rate) to provide natural-like double-stranded targets. As such, in some embodiments, annealing provides double stranded oligonucleotides comprising sequences from wild-type ACTB, KRAS, BMP3, and NDRG4; sequences from KRAS mutant 38A and KRAS mutant 35C; and from methylated BMP3 and methylated NDRG4. Then, in some embodiments, control formulations (e.g., a DNA control reagent) are produced by mixing the double stranded targets at the desired concentrations to produce the desired signal (e.g., see above) in a buffer (e.g., 80% DNA Stabilization Buffer (500 mM Tris, 150 mM EDTA, and 10 mM NaCl, pH 9) plus 50 ng/mL fish DNA). In some embodiments, controls are provided as a High, Low, and/or Negative control. Compositions and concentrations of the components for these controls are provided in Table 23, Table 24, Table 25, and/or FIG. 9.

Although the disclosure herein refers to certain illustrated embodiments, it is to be understood that these embodiments are presented by way of example and not by way of limitation. All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in molecular biology, biology, chemistry, biochemistry, medical sciences, or related fields are intended to be within the scope of the following claims.

We claim:

1. A run control composition, comprising:

a) a number of copies of a first synthetic DNA fragment comprising a sequence of a portion of a human biomarker DNA, wherein the sequence is synthesized to comprise a sequence region containing a number and pattern of cytosines and cytosine-phosphate-guanosine (CpG) dinucleotides in which each of the cytosines in the CpG dinucleotides in the pattern comprises a 5-methyl;

b) a number of copies of a second synthetic DNA fragment comprising the same sequence of the same portion of the human biomarker DNA as the first synthetic DNA, and comprising a sequence region comprising the same number and pattern of cytosines and CpG dinucleotides as the sequence region in the first synthetic DNA fragment, wherein none of the cytosines in the pattern comprises a 5-methyl; and c) fish DNA.

2. The run control composition of claim 1, wherein the first synthetic DNA fragment and the second synthetic DNA fragment are double-stranded.

3. The run control composition of claim 1, wherein the first and second synthetic DNA fragments each further comprise a second sequence region containing a CpG dinucleotide in which the cytosine does not comprise a 5-methyl.

4. The run control composition of claim 1, wherein the composition comprises at least 50 μg/mL fish DNA.

5. The run control composition of claim 1, further comprising a DNA stabilization buffer comprising Tris-HCl, EDTA, and NaCl.

6. The run control composition of claim 5, wherein the DNA stabilization buffer is 80% of the volume of the composition, and wherein the DNA stabilization buffer comprises 500 mM Tris-HCl, 150 mM EDTA, and 10 mM NaCl, pH 9.

7. The run control composition of claim 1, further comprising a synthetic DNA fragment comprising a sequence from a human reference gene.

* * * * *

SEQUENCE LISTING

```
<160> NUMBER OF SEQ ID NOS: 18

<210> SEQ ID NO 1
<211> LENGTH: 154
<212> TYPE: DNA
<213> ORGANISM: Artificial sequence
<220> FEATURE:
<223> OTHER INFORMATION: Synthetic

<400> SEQUENCE: 1
```

```
acattttcat tatttttatt ataaggcctg ctgaaaatga ctgaatataa acttgtggta     60

gttggagctg gtgacgtagg caagagtgcc ttgacgatac agctaattca gaatcatttt    120

gtggacgaat atgatccaac aatagaggta aatc                                154


<210> SEQ ID NO 2
<211> LENGTH: 154
<212> TYPE: DNA
<213> ORGANISM: Artificial sequence
<220> FEATURE:
<223> OTHER INFORMATION: Synthetic

<400> SEQUENCE: 2

gatttacctc tattgttgga tcatattcgt ccacaaaatg attctgaatt agctgtatcg     60

tcaaggcact cttgcctacg tcaccagctc caactaccac aagtttatat tcagtcattt    120

tcagcaggcc ttataataaa aataatgaaa atgt                                154


<210> SEQ ID NO 3
<211> LENGTH: 154
<212> TYPE: DNA
<213> ORGANISM: Artificial sequence
<220> FEATURE:
<223> OTHER INFORMATION: Synthetic

<400> SEQUENCE: 3

acattttcat tatttttatt ataaggcctg ctgaaaatga ctgaatataa acttgtggta     60

gttggagctg ctggcgtagg caagagtgcc ttgacgatac agctaattca gaatcatttt    120

gtggacgaat atgatccaac aatagaggta aatc                                154


<210> SEQ ID NO 4
<211> LENGTH: 154
<212> TYPE: DNA
<213> ORGANISM: Artificial sequence
<220> FEATURE:
<223> OTHER INFORMATION: Synthetic

<400> SEQUENCE: 4

gatttacctc tattgttgga tcatattcgt ccacaaaatg attctgaatt agctgtatcg     60

tcaaggcact cttgcctacg ccagcagctc caactaccac aagtttatat tcagtcattt    120

tcagcaggcc ttataataaa aataatgaaa atgt                                154


<210> SEQ ID NO 5
<211> LENGTH: 126
<212> TYPE: DNA
<213> ORGANISM: Artificial sequence
<220> FEATURE:
<223> OTHER INFORMATION: Synthetic

<400> SEQUENCE: 5

tttgtctctc tgactaggtg tctaagacag tgttgtgggt gtaggtacta acactggctc     60

gtgtgacaag gccatgaggc tggtgtaaag cggccttgga gtgtgtatta agtaggtgca    120

cagtag                                                               126


<210> SEQ ID NO 6
<211> LENGTH: 126
<212> TYPE: DNA
<213> ORGANISM: Artificial sequence
<220> FEATURE:
<223> OTHER INFORMATION: Synthetic
```

<400> SEQUENCE: 6
ctactgtgca cctacttaat acacactcca aggccgcttt acaccagcct catggccttg 60
tcacacgagc cagtgttagt acctacaccc acaacactgt cttagacacc tagtcagaga 120
gacaaa 126

<210> SEQ ID NO 7
<211> LENGTH: 154
<212> TYPE: DNA
<213> ORGANISM: Artificial sequence
<220> FEATURE:
<223> OTHER INFORMATION: Synthetic

<400> SEQUENCE: 7
acattttcat tatttttatt ataaggcctg ctgaaaatga ctgaatataa acttgtggta 60
gttggagctg gtggcgtagg caagagtgcc ttgacgatac agctaattca gaatcatttt 120
gtggacgaat atgatccaac aatagaggta aatc 154

<210> SEQ ID NO 8
<211> LENGTH: 154
<212> TYPE: DNA
<213> ORGANISM: Artificial sequence
<220> FEATURE:
<223> OTHER INFORMATION: Synthetic

<400> SEQUENCE: 8
gatttacctc tattgttgga tcatattcgt ccacaaaatg attctgaatt agctgtatcg 60
tcaaggcact cttgcctacg ccaccagctc caactaccac aagtttatat tcagtcattt 120
tcagcaggcc ttataataaa aataatgaaa atgt 154

<210> SEQ ID NO 9
<211> LENGTH: 126
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (25)..(25)
<223> OTHER INFORMATION: N=5-Me-dC
<220> FEATURE:
<221> NAME/KEY: misc_feature
<222> LOCATION: (31)..(31)
<223> OTHER INFORMATION: N=5-Me-dC
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (35)..(35)
<223> OTHER INFORMATION: N=5-Me-dC
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (44)..(44)
<223> OTHER INFORMATION: N=5-Me-dC
<220> FEATURE:
<221> NAME/KEY: misc_feature
<222> LOCATION: (48)..(48)
<223> OTHER INFORMATION: N=5-Me-dC
<220> FEATURE:
<221> NAME/KEY: misc_feature
<222> LOCATION: (55)..(55)
<223> OTHER INFORMATION: N=5-Me-dC
<220> FEATURE:
<221> NAME/KEY: misc_feature
<222> LOCATION: (68)..(68)
<223> OTHER INFORMATION: N=5-Me-dC
<220> FEATURE:
<221> NAME/KEY: misc_feature
<222> LOCATION: (70)..(70)
<223> OTHER INFORMATION: N=5-Me-dC
<220> FEATURE:
<221> NAME/KEY: misc_feature
<222> LOCATION: (79)..(79)
<223> OTHER INFORMATION: N=5-Me-dC
<220> FEATURE:
<221> NAME/KEY: misc_feature
<222> LOCATION: (88)..(88)
<223> OTHER INFORMATION: N=5-Me-dC
<220> FEATURE:
<221> NAME/KEY: misc_feature
<222> LOCATION: (90)..(90)
<223> OTHER INFORMATION: N=5-Me-dC
<220> FEATURE:
<221> NAME/KEY: misc_feature
<222> LOCATION: (92)..(92)
<223> OTHER INFORMATION: N=5-Me-dC

<400> SEQUENCE: 9
gggtgtcccc caggctccgc gtcgnggtcc cngctngccc tccngccngc ccacngggca 60
ccccagcngn gcagaaggng gaagccangn gngagggacc gcggtccgtc cgggactagc 120
cccagg 126

<210> SEQ ID NO 10
<211> LENGTH: 126
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (34)..(34)
<223> OTHER INFORMATION: N=5-Me-dC
<220> FEATURE:
<221> NAME/KEY: misc_feature
<222> LOCATION: (36)..(36)
<223> OTHER INFORMATION: N=5-Me-dC
<220> FEATURE:
<221> NAME/KEY: misc_feature
<222> LOCATION: (38)..(38)
<223> OTHER INFORMATION: N=5-Me-dC
<220> FEATURE:
<221> NAME/KEY: misc_feature
<222> LOCATION: (47)..(47)
<223> OTHER INFORMATION: N=5-Me-dC
<220> FEATURE:
<221> NAME/KEY: misc_feature
<222> LOCATION: (56)..(56)
<223> OTHER INFORMATION: N=5-Me-dC
<220> FEATURE:
<221> NAME/KEY: misc_feature
<222> LOCATION: (58)..(58)
<223> OTHER INFORMATION: N=5-Me-dC
<220> FEATURE:
<221> NAME/KEY: misc_feature
<222> LOCATION: (71)..(71)
<223> OTHER INFORMATION: N=5-Me-dC
<220> FEATURE:
<221> NAME/KEY: misc_feature
<222> LOCATION: (78)..(78)
<223> OTHER INFORMATION: N=5-Me-dC
<220> FEATURE:
<221> NAME/KEY: misc_feature
<222> LOCATION: (82)..(82)
<223> OTHER INFORMATION: N=5-Me-dC
<220> FEATURE:
<221> NAME/KEY: misc_feature
<222> LOCATION: (90)..(90)

<223> OTHER INFORMATION: N=5-Me-dC
<220> FEATURE:
<221> NAME/KEY: misc_feature
<222> LOCATION: (94)..(94)
<223> OTHER INFORMATION: N=5-Me-dC
<220> FEATURE:
<221> NAME/KEY: misc_feature
<222> LOCATION: (101)..(101)
<223> OTHER INFORMATION: N=5-Me-dC

<400> SEQUENCE: 10
cctggggcta gtcccggacg gaccgcggtc cctngngngt ggcttcngcc ttctgngngg 60
ctggggtgcc nggtgggngg gngggagggn gagnggggac ngcgacgcgg agcctggggg 120
acaccc 126

<210> SEQ ID NO 11
<211> LENGTH: 126
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (46)..(46)
<223> OTHER INFORMATION: N=5-Me-dC
<220> FEATURE:
<221> NAME/KEY: misc_feature
<222> LOCATION: (52)..(52)
<223> OTHER INFORMATION: N=5-Me-dC
<220> FEATURE:
<221> NAME/KEY: misc_feature
<222> LOCATION: (55)..(55)
<223> OTHER INFORMATION: N=5-Me-dC
<220> FEATURE:
<221> NAME/KEY: misc_feature
<222> LOCATION: (58)..(58)
<223> OTHER INFORMATION: N=5-Me-dC
<220> FEATURE:
<221> NAME/KEY: misc_feature
<222> LOCATION: (68)..(68)
<223> OTHER INFORMATION: N=5-Me-dC
<220> FEATURE:
<221> NAME/KEY: misc_feature
<222> LOCATION: (74)..(74)
<223> OTHER INFORMATION: N=5-Me-dC
<220> FEATURE:
<221> NAME/KEY: misc_feature
<222> LOCATION: (84)..(84)
<223> OTHER INFORMATION: N=5-Me-dC
<220> FEATURE:
<221> NAME/KEY: misc_feature
<222> LOCATION: (89)..(89)
<223> OTHER INFORMATION: N=5-Me-dC

<400> SEQUENCE: 11
cgggctccgt gcgccctcgc cccagctggt ttggagttca accctnggct cngcngcngg 60
ctccttgngc cttnggagtg tccngcagng acgccgggag ccgacgcgcc gcgcgggtac 120
ctagcc 126

<210> SEQ ID NO 12
<211> LENGTH: 126
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (37)..(37)
<223> OTHER INFORMATION: N=5-Me-dC
<220> FEATURE:
<221> NAME/KEY: misc_feature
<222> LOCATION: (42)..(42)
<223> OTHER INFORMATION: N=5-Me-dC
<220> FEATURE:
<221> NAME/KEY: misc_feature
<222> LOCATION: (52)..(52)
<223> OTHER INFORMATION: N=5-Me-dC
<220> FEATURE:
<221> NAME/KEY: misc_feature
<222> LOCATION: (58)..(58)
<223> OTHER INFORMATION: N=5-Me-dC
<220> FEATURE:
<221> NAME/KEY: misc_feature
<222> LOCATION: (68)..(68)
<223> OTHER INFORMATION: N=5-Me-dC
<220> FEATURE:
<221> NAME/KEY: misc_feature
<222> LOCATION: (71)..(71)
<223> OTHER INFORMATION: N=5-Me-dC
<220> FEATURE:
<221> NAME/KEY: misc_feature
<222> LOCATION: (74)..(74)
<223> OTHER INFORMATION: N=5-Me-dC
<220> FEATURE:
<221> NAME/KEY: misc_feature
<222> LOCATION: (80)..(80)
<223> OTHER INFORMATION: N=5-Me-dC

<400> SEQUENCE: 12
ggctaggtac ccgcgcggcg cgtcggctcc cggcgtngct gngggacact cngaaggngc 60
aaggagcngg nggnggagcn gagggttgaa ctccaaacca gctggggcga gggcgcacgg 120
agcccg 126

<210> SEQ ID NO 13
<211> LENGTH: 126
<212> TYPE: DNA
<213> ORGANISM: Artificial sequence
<220> FEATURE:
<223> OTHER INFORMATION: Synthetic

<400> SEQUENCE: 13
gggtgtcccc caggctccgc gtcgcggtcc ccgctcgccc tcccgcccgc ccaccgggca 60
ccccagccgc gcagaaggcg gaagccacgc gcgagggacc gcggtccgtc cgggactagc 120
cccagg 126

<210> SEQ ID NO 14
<211> LENGTH: 126
<212> TYPE: DNA
<213> ORGANISM: Artificial sequence
<220> FEATURE:
<223> OTHER INFORMATION: Synthetic

<400> SEQUENCE: 14
cctggggcta gtcccggacg gaccgcggtc cctcgcgcgt ggcttccgcc ttctgcgcgg 60
ctggggtgcc cggtgggcgg gcgggagggc gagcggggac cgcgacgcgg agcctggggg 120
acaccc 126

<210> SEQ ID NO 15
<211> LENGTH: 126
<212> TYPE: DNA
<213> ORGANISM: Artificial sequence
<220> FEATURE:
<223> OTHER INFORMATION: Synthetic

<400> SEQUENCE: 15
cgggctccgt gcgccctcgc cccagctggt ttggagttca accctcggct ccgccgccgg 60
ctccttgcgc cttcggagtg tcccgcagcg acgccgggag ccgacgcgcc gcgcgggtac 120
ctagcc 126

<210> SEQ ID NO 16
<211> LENGTH: 126
<212> TYPE: DNA
<213> ORGANISM: Artificial sequence
<220> FEATURE:
<223> OTHER INFORMATION: Synthetic

<400> SEQUENCE: 16
ggctaggtac ccgcgcggcg cgtcggctcc cggcgtcgct gcgggacact ccgaaggcgc 60
aaggagccgg cggcggagcc gagggttgaa ctccaaacca gctggggcga gggcgcacgg 120
agcccg 126

<210> SEQ ID NO 17
<211> LENGTH: 55
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (11)..(11)
<223> OTHER INFORMATION: N=i-methyl-dC
<220> FEATURE:
<221> NAME/KEY: misc_feature
<222> LOCATION: (17)..(17)
<223> OTHER INFORMATION: N=i-methyl-dC
<220> FEATURE:
<221> NAME/KEY: misc_feature
<222> LOCATION: (20)..(20)
<223> OTHER INFORMATION: N=i-methyl-dC
<220> FEATURE:
<221> NAME/KEY: misc_feature
<222> LOCATION: (23)..(23)
<223> OTHER INFORMATION: N=i-methyl-dC
<220> FEATURE:
<221> NAME/KEY: misc_feature
<222> LOCATION: (33)..(33)
<223> OTHER INFORMATION: N=i-methyl-dC
<220> FEATURE:
<221> NAME/KEY: misc_feature
<222> LOCATION: (39)..(39)
<223> OTHER INFORMATION: N=i-methyl-dC
<220> FEATURE:
<221> NAME/KEY: misc_feature
<222> LOCATION: (49)..(49)
<223> OTHER INFORMATION: N=i-methyl-dC
<220> FEATURE:
<221> NAME/KEY: misc_feature
<222> LOCATION: (54)..(54)
<223> OTHER INFORMATION: N=i-methyl-dC

<400> SEQUENCE: 17
gttcaaccct nggctcngcn gcnggctcct tgngccttng gagtgtccng cagng 55

<210> SEQ ID NO 18
<211> LENGTH: 55
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: N=i-methyl-dC
<220> FEATURE:
<221> NAME/KEY: misc_feature
<222> LOCATION: (6)..(6)
<223> OTHER INFORMATION: N=i-methyl-dC -continued

```
<220> FEATURE:
<221> NAME/KEY: misc_feature
<222> LOCATION: (16)..(16)
<223> OTHER INFORMATION: N=i-methyl-dC
<220> FEATURE:
<221> NAME/KEY: misc_feature
<222> LOCATION: (22)..(22)
<223> OTHER INFORMATION: N=i-methyl-dC
<220> FEATURE:
<221> NAME/KEY: misc_feature
<222> LOCATION: (32)..(32)
<223> OTHER INFORMATION: N=i-methyl-dC
<220> FEATURE:
<221> NAME/KEY: misc_feature
<222> LOCATION: (35)..(35)
<223> OTHER INFORMATION: N=i-methyl-dC
<220> FEATURE:
<221> NAME/KEY: misc_feature
<222> LOCATION: (38)..(38)
<223> OTHER INFORMATION: N=i-methyl-dC
<220> FEATURE:
<221> NAME/KEY: misc_feature
<222> LOCATION: (44)..(44)
<223> OTHER INFORMATION: N=i-methyl-dC

<400> SEQUENCE: 18

ngctgnggga cactcngaag gngcaaggag cnggnggngg agcngagggt tgaac          55
```